US009321742B2

(12) United States Patent
Kim et al.

(10) Patent No.: US 9,321,742 B2
(45) Date of Patent: Apr. 26, 2016

(54) N1-CYCLIC AMINE-N5-SUBSTITUTED BIGUANIDE DERIVATIVES, METHODS OF PREPARING THE SAME AND PHARMACEUTICAL COMPOSITION COMPRISING THE SAME

(75) Inventors: Sung Wuk Kim, Seongnam-si (KR); Chang Hee Min, Seoul (KR); Se Hwan Park, Daejeon (KR); Duck Kim, Daegu (KR); Ji Sun Lee, Daejeon (KR); Yong Eun Kim, Daejeon (KR); Ju Hoon Oh, Gangneung-Si (KR)

(73) Assignee: IMMUNOMET THERAPEUTICS INC., Cambridge, MA (US)

( * ) Notice: Subject to any disclaimer, the term of this patent is extended or adjusted under 35 U.S.C. 154(b) by 0 days.

(21) Appl. No.: 14/237,546

(22) PCT Filed: Aug. 8, 2012

(86) PCT No.: PCT/KR2012/006327
§ 371 (c)(1),
(2), (4) Date: Feb. 6, 2014

(87) PCT Pub. No.: WO2013/022279
PCT Pub. Date: Feb. 14, 2013

(65) Prior Publication Data
US 2014/0179661 A1 Jun. 26, 2014

(30) Foreign Application Priority Data

Aug. 8, 2011 (KR) .................. 10-2011-0078762
Sep. 2, 2011 (KR) .................. 10-2011-0089267

(51) Int. Cl.
| C07C 279/26 | (2006.01) |
| C07C 29/16 | (2006.01) |
| C07D 205/04 | (2006.01) |
| C07D 213/40 | (2006.01) |
| C07D 295/215 | (2006.01) |
| C07D 333/20 | (2006.01) |
| C07D 307/52 | (2006.01) |

(52) U.S. Cl.
CPC .......... *C07D 295/215* (2013.01); *C07D 205/04* (2013.01); *C07D 213/40* (2013.01); *C07D 307/52* (2013.01); *C07D 333/20* (2013.01)

(58) Field of Classification Search
None
See application file for complete search history.

(56) References Cited

U.S. PATENT DOCUMENTS

| 2,467,371 A | * | 4/1949 | Curd et al. .................... 564/234 |
| 2,951,843 A | | 9/1960 | Haack et al. |
| 3,519,644 A | | 7/1970 | Schenker et al. |
| 3,960,949 A | | 6/1976 | Ahrens et al. |
| 5,258,513 A | * | 11/1993 | Van Keulen et al. ......... 544/58.2 |
| 5,348,956 A | * | 9/1994 | Van Keulen et al. ....... 514/232.2 |

FOREIGN PATENT DOCUMENTS

| EP | 0527117 A1 | 2/1993 |
| EP | 527117 A1 * | 2/1993 |
| EP | 2332925 A1 | 6/2011 |
| KR | 1020030029050 A | 4/2003 |
| WO | WO-2009113092 A2 | 9/2009 |
| WO | 2011083998 A2 | 7/2011 |

OTHER PUBLICATIONS

Leroux et al Bioorg. & Medicinal Chemistry (1999), 7(3), 509-516.*
Zakikhani et al. "Metformin is an AMP Kinase-Dependent Growth Inhibitor for Breast Cancer Cells." *Cancer Res.* 66(2006):10269-10273.
Curd, F.H.S. et al., "Synthetic Antimalarials. Part X. Some Aryldiguanide ('-biguanide') Derivatives," Journal of the American Chemical Society, pp. 729-737 (1946).
James, John W. et al., "The Synthesis of Some Heterocyclic Derivatives of Biguanide with Antibacterial Activity," Journal of Medicinal Chemistry, vol. 11:942-945 (1968).
Database Registry Accession No. 705915-51-1, Chemical Abstracts Service, 1 page, Jul. 7, 2004.
Database Registry Accession No. 802011-34-3, Chemical Abstracts Service, 1 page, Dec. 23, 2004.

* cited by examiner

*Primary Examiner* — Nyeemah A Grazier
(74) *Attorney, Agent, or Firm* — Mintz Levin Cohn Ferris Glovsky and Popeo, P.C.; Fred C. Hernandez; Linyu L. Mitra

(57) ABSTRACT

A N1-cyclic amine-N5-substituted biguanide derivative of Formula 1 or a pharmaceutically acceptable salt thereof, a method of manufacturing the same, and a pharmaceutical composition including the biguanide derivative or the pharmaceutically acceptable salt thereof as an active ingredient are provided. The biguanide derivatives have an effect of inhibiting cancer cell proliferation and also exhibit anticancer activity including inhibition of cancer metastasis and cancer recurrence, because they are effective in activating AMPK, which is associated with the control of energy metabolism, even when administered in a small dose compared with conventional drugs. Also, the biguanide derivatives are highly effective at lowering blood glucose and lipid concentration by AMPK activation, thus they may be effectively used to treat diabetes mellitus, obesity, hyperlipemia, hypercholesterolemia, fatty liver, coronary artery disease, osteoporosis, polycystic ovary syndrome and metabolic syndrome.

15 Claims, No Drawings

N1-CYCLIC AMINE-N5-SUBSTITUTED BIGUANIDE DERIVATIVES, METHODS OF PREPARING THE SAME AND PHARMACEUTICAL COMPOSITION COMPRISING THE SAME

CROSS-REFERENCE TO RELATED APPLICATIONS

This application is a national stage application, filed under 35 U.S.C. §371, of International Application No. PCT/KR2012/006327, filed Aug. 8, 2012, which claims priority to and the benefit of Korean Patent Application No. 10-2011-0089267, filed Sep. 2, 2011, and Korean Patent Application No. 10-2011-0078762, filed Aug. 8, 2011, the contents of each of which are incorporated herein by reference in their entireties.

TECHNICAL FIELD

The present invention relates to an N1-cyclic amine-N5-substituted biguanide derivative that inhibits cancer cell proliferation, cancer metastasis and cancer recurrence and exhibits excellent effects in treatment of diabetes mellitus and metabolic diseases by activation of 5'-AMP-activated protein kinase (AMPK), even when administered in a small dose compared with conventional drugs, a method of preparing the same, and a pharmaceutical composition comprising the N1-cyclic amine-N5-substituted biguanide derivative as an active ingredient.

BACKGROUND ART

AMPK (AMP-activated protein kinase) is an enzyme that functions to control a metabolic pathway so as to maintain balance between supply of nutrients and demand for energy, and thus maintain energy homeostasis in cells and the whole body. AMPK is activated as the ratio of AMP/ATP in the cells increases due to a hypoxemic state or glucose deficiency. The activated AMPK induces fatty acid oxidation to produce a larger amount of ATP and inhibits anabolisms requiring the use of ATP. Also, AMPK activation enhances sensitivity to insulin, inhibits glucose generation in the liver, and improves glucose absorption in the muscles. Due to its actions, AMPK has been regarded as a desirable target for treatment of type II diabetes mellitus and metabolic diseases. AMPK inhibits proliferation of cancer cells and kills cancer cells by regulating energy metabolism in the cancer cells as well as in normal cells. AMPK activated in cancer cells shows an anticancer activity by phosphorylating mTORC1, p53, fatty acid synthase and the like to regulate the cell cycle, cell polarity, autophagy, apoptosis, etc.

Metformin has been used to treat insulin-independent diabetes mellitus (i.e., type II diabetes mellitus) since it is most effective at lowering blood glucose, does not develop hypoglycemia or hyperinsulinemia and can prevent complications among oral therapeutic agents for treating diabetes mellitus. In recent years, metformin has been extensively researched. Also, it was reported that metformin activates AMP-activated protein kinase (AMPK) by inhibiting the action of complex 1 of the electron transport system in the mitochondria to obstruct intracellular generation of energy and inhibits activation of the mTOR/S6K1 signaling pathway in which proteins essential for survival are produced to obstruct proliferation of cancer cells and tumor growth (Mol. Cancer Ther. 9(5): 1092-1099 (2010)). Consequently, metformin has received considerable attention as an anticancer agent for regulating cancer cell metabolism. Also, an epidemiological survey confirmed that the incidence of cancer and mortality by cancer were lowered for patients treated with metformin (BMJ.330: 1304-1305 (2005)).

Meanwhile, there is increasing clinical evidence indicating that cancer stem cells take part in recurrence and metastasis of cancer. The cancer stem cells refer to cancer cells that have self-regeneration or differentiation capacity which is characteristically innate to stem cells. The cancer stem cells are present in the cancer tissue at a content of 0.2% or less, and are characterized by their slow proliferation. Since lots of anticancer agents developed so far target cancer cells that proliferate rapidly, the cancer stem cells are resistant to conventional anticancer therapy when cancer stem cells are treated with the anticancer agents, thereby causing poor prognoses. On the other hand, it was reported that metformin prevents the recurrence of cancer as it selectively acts on cancer stem cells among breast cancer cells and removes the cancer stem cells (Cancer Res. 69(19): 7507-11 (2009)).

Also, it was found that metformin prevents the metastasis of cancer by interfering with the motility and invasion of the cancer cells since it inhibits the expression of Snail 1, Slug, Twist, ZEB 1/2 and TGF-β, which are transcription factors associated with the epithelial-to-mesenchymal transition (EMT), and promotes the expression of E-cadherin to prevent cancer cells from leading to the EMT (Cell Cycle 10: 7, 1144-1151 (2011), Cell Cycle 9: 18, 3807-3814 (2010), Cell Cycle 9: 22, 4461-4468 (2010)).

However, metformin is generally administered three times a day, with a single dose of approximately 500 mg or more. Thus, a tablet that can contain approximately 1,500 mg or more of metformin is required in order to prepare metformin in the form of a sustained released tablet to be administered once a day. In this case, the tablet is too large for patients to swallow. In addition, since one tablet of a sustained-release preparation currently available on the market contains only approximately 750 mg of metformin, two or more tablets of the sustained-release preparation should be taken. Also, the use of phenformin, which belongs to the same group of biguanides, has been completely prohibited since the late 1970s due to its severe side effects such as lactic acidosis.

For these reasons, there is a need for a biguanide-based substance that exhibits better pharmacological action than the conventional metformin and has improved physiochemical properties without the side effects of phenformin.

DISCLOSURE OF INVENTION

Technical Problem

The present invention is directed to providing a novel biguanide derivative that is highly effective in inhibiting proliferation of cancer cells, cancer metastasis and cancer recurrence, even when administered in a small dose compared with conventional drugs, or a pharmaceutically acceptable salt thereof, and a method of preparing the same.

Also, the present invention is directed to providing a pharmaceutical composition including the above-mentioned compound as an active ingredient that is highly effective at lowering blood glucose and lipid concentration so as to prevent or treat diabetes mellitus, obesity, hyperlipemia, fatty liver, hypercholesterolemia, a coronary artery disease, osteoporosis, polycystic ovary syndrome, metabolic syndrome, etc.

Solution to Problem

One aspect of the present invention provides an N1-cyclic amine-N5-substituted biguanide derivative compound of Formula 1, or a pharmaceutically acceptable salt thereof:

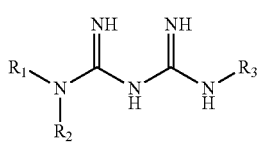

[Formula 1]

In Formula 1, $R_1$ and $R_2$ are taken together with nitrogen to which they are attached to form 3- to 8-membered heterocycloalkyl, $R_3$ is $C_{3-7}$ cycloalkyl; or $C_{1-12}$ alkyl unsubstituted or substituted with $C_{3-12}$ aryl or $C_{3-12}$ heteroaryl, wherein $C_{3-7}$ cycloalkyl, 3- to 8-membered heterocycloalkyl, $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

In this specification, a "substituted" group refers to a group in which at least one hydrogen atom is replaced with at least one non-hydrogen atom group, provided that the group satisfies the valence electron requirements and forms a chemically stable compound from the substitution. Unless explicitly described as "unsubstituted" in this specification, it should be understood that all substituents will be unsubstituted or substituted with another substituent. The substituents $R_1$ to $R_3$ on the biguanide derivative according to the present invention may each be re-substituted with at least one of the above-defined substituents.

The term "halogen" or "halo" refers to fluoro, chloro, bromo, and iodo.

The term "hydroxy" refers to —OH.

The term "alkyl" refers to a linear and branched saturated hydrocarbon group generally having a specified number of atoms (for example, 1 to 12 atoms). Examples of the alkyl group include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth1-yl, n-hexyl, n-heptyl and n-octyl. The alkyl may be attached to a parent group or a substrate at any ring atom, unless the attachment would violate valence electron requirements. Likewise, the alkyl group may include at least one non-hydrogen substituent unless the substitution would violate valence electron requirements. For example, the term "haloalkyl" refers to a group such as —CH$_2$(halo), —CH(halo)$_2$ or C(halo)$_3$, meaning a methyl group in which at least one hydrogen atom is replaced with halogen. Examples of the term "haloalkyl" group include, without limitation, trifluoromethyl, trichloromethyl, tribromomethyl and tri-iodomethyl.

The term "alkoxy" refers to alkyl-O—, provided that the alkyl is the same as defined above. Examples of the alkoxy group include, without limitation, methoxy, ethoxy, n-propoxy, i-propoxy, n-butoxy, s-butoxy, t-butoxy, n-pentoxy, s-pentoxy, etc. The alkoxy may be attached to a parent group or a substrate at any ring atom, unless the attachment would violate valence electron requirements. Likewise, the alkoxy group may include at least one non-hydrogen substituent unless the attachment would violate valence electron requirements. For example, the term "haloalkoxy" refers to —O—CH$_2$ (halo), —O—CH(halo)$_2$ or —O—C(halo)$_3$, meaning a methyl group in which at least one hydrogen atom is replaced with halogen. Examples of the term "haloalkoxy" group include, without limitation, trifluoromethoxy, trichloromethoxy, tribromomethoxy and triiodomethoxy.

The term "cycloalkyl" refers to a saturated monocyclic and dicyclic hydrocarbon ring generally having the specified number of atoms that include a ring (for example, $C_{3-8}$ cycloalkyl refers to a cycloalkyl group having 3, 4, 5, 6, 7 or 8 carbon atoms as a ring member). The cycloalkyl may be attached to a parent or substrate at any ring atom, unless the attachment would violate valence electron requirements. Likewise, the cycloalkyl group may include at least one non-hydrogen substituent unless the substitution would violate valence electron requirements.

The term "heterocycloalkyl" refers to a monocyclic and dicyclic hydrocarbon ring having 3- to 12-membered ring atoms containing 1 to 3 heteroatoms independently selected from nitrogen, oxygen and sulfur. The heterocycloalkyl may be attached to a parent or substrate at any ring atom, unless the attachment would violate valence electron requirements. Likewise, the heterocycloalkyl group may include at least one non-hydrogen substituent unless the substitution would violate valence electron requirements. Examples of the heterocycloalkyl group include, without limitation, aziridine, azetidine, imidazolyl, pyrrolyl, pyrrolidinyl, piperidyl, morpholinyl, piperazinyl, azepanyl, indolyl, indolinyl, etc.

The term "aryl" refers to monovalent and bivalent aromatic groups, respectively including 5- and 6-membered monocyclic aromatic groups and "heteroaryl" refers to monovalent and bivalent aromatic groups, respectively including 5- and 6-membered monocyclic aromatic groups that contain 1 to 4 heteroatoms independently selected from nitrogen, oxygen and sulfur.

Examples of the "heteroaryl" group include, without limitation, furanyl, pyrrolyl, thiophenyl, thiazolyl, isothiazolyl, imidazolyl, triazolyl, tetrazolyl, pyrazolyl, oxazolyl, isooxazolyl, pyridinyl, pyrazinyl, pyridazinyl, pyrimidinyl, isoquinolinyl, carbazolyl, benzoxazolyl, benzodioxazolyl, benzothiazolyl, benzimidazolyl, benzothiophenyl, triazinyl, phthalazinyl, quinolinyl, indolyl, benzofuranyl, furinyl and indolizinyl.

According to another exemplary embodiment, $R_1$ and $R_2$ may be taken together with nitrogen to which they are attached to form 4- to 7-membered heterocycloalkyl, $R_3$ may be $C_{3-7}$ cycloalkyl; or $C_{1-12}$ alkyl unsubstituted or substituted with $C_{3-12}$ aryl or $C_{3-12}$ heteroaryl, wherein $C_{3-7}$ cycloalkyl, 4- to 7-membered heterocycloalkyl, $C_{3-12}$ aryl or $C_{3-12}$ heteroaryl may be unsubstituted or substituted with at least one non-hydrogen substituent selected from the group consisting of halogen, $C_{1-4}$ alkyl and $C_{1-4}$ alkoxy, and the non-hydrogen substituent may be unsubstituted or further substituted with halogen.

According to one exemplary embodiment, $C_{3-12}$ aryl may be a phenyl or naphthalenyl, $C_{3-12}$ heteroaryl may be a furanyl, thiophenyl, pyridinyl, pyrrolyl, imidazolyl or pyrimidinyl, $C_{3-12}$ aryl or $C_{3-12}$ heteroaryl may be unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

According to another exemplary embodiment, $R_1$ and $R_2$ may be taken together with nitrogen to which they are attached to form 3- to 8-membered heterocycloalkyl selected from the group consisting of azetidinyl, pyrrolidinyl, piperidinyl, morpholinyl, piperazinyl, azepanyl and aziridinyl, $R_3$ may be $C_{3-7}$ cycloalkyl; or $C_{1-12}$ alkyl unsubstituted or substituted with $C_{3-12}$ aryl or $C_{3-12}$heteroaryl, wherein $C_{3-7}$ cycloalkyl, 3- to 8-membered heterocycloalkyl, $C_{3-12}$ aryl or $C_{3-12}$ heteroaryl may be unsubstituted or substituted with at least one non-hydrogen substituent selected from the group consisting of halogen, $C_{1-4}$ alkyl and $C_{1-4}$ alkoxy, and the non-hydrogen substituent may be unsubstituted or further substituted with halogen.

According to still another exemplary embodiment, the present invention provides the compound of Formula 1 or the pharmaceutically acceptable salt thereof as follows, $R_1$ and $R_2$ are taken together with nitrogen to which they are attached to form 3- to 8-membered heterocycloalkyl selected from the group consisting of azetidinyl, pyrrolidinyl, piperidinyl, morpholinyl, piperazinyl, azepanyl and aziridinyl, $R_3$ is $C_{3-7}$ cycloalkyl; or $C_{1-12}$ alkyl that is unsubstituted or substituted with $C_{3-12}$ aryl or $C_{3-12}$ heteroaryl which is selected from the group consisting of a phenyl, naphthalenyl, furanyl, thiophenyl, pyridinyl, pyrrolyl and imidazolyl, wherein 3- to 8-membered heterocycloalkyl, $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

According to still another exemplary embodiment, $R_1$ and $R_2$ may be taken together with nitrogen to which they are attached to form 4- to 7-membered heterocycloalkyl selected from the group consisting of azetidinyl, pyrrolidinyl, piperidinyl, morpholinyl, piperazinyl and azepanyl, $R_3$ may be $C_{3-7}$ cycloalkyl; or $C_{1-12}$ alkyl that is unsubstituted or substituted with $C_{3-12}$ aryl or $C_{3-12}$ heteroaryl which is selected from the group consisting of a phenyl, naphthalenyl, furanyl, thiophenyl and pyridinyl, wherein 4- to 7-membered heterocycloalkyl, $C_{3-12}$ aryl or $C_{3-12}$ heteroaryl may be unsubstituted or substituted with at least one non-hydrogen substituent selected from the group consisting of halogen, $C_{1-4}$ alkyl and $C_{1-4}$ alkoxy, and the non-hydrogen substituent may be unsubstituted or further substituted with halogen.

According to still another exemplary embodiment, the present invention provides the compound of Formula 1 or the pharmaceutically acceptable salt thereof as follows, $R_1$ and $R_2$ are taken together with nitrogen to which they are attached to form 4- to 7-membered heterocycloalkyl selected from the group consisting of azetidinyl, pyrrolidinyl, piperidinyl, morpholinyl, piperazinyl and azepanyl, wherein piperazinyl is substituted with $C_{1-6}$alkyl, $R_3$ is $C_{4-7}$ cycloalkyl; or $C_{1-6}$ alkyl that is unsubstituted or substituted with $C_{3-12}$ aryl or $C_{3-12}$ heteroaryl which is selected from the group consisting of a phenyl, naphthalenyl, furanyl, thiophenyl and pyridinyl, wherein $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, haloalkyl and haloalkoxy.

According to one exemplary embodiment, the compound of Formula 1 may be N1-piperidine-N5-(3-trifluoromethyl) benzyl biguanide; N1-piperidine-N5-methyl biguanide; N1-piperidine-N5-propyl biguanide; N1-piperidine-N5-isopropyl biguanide; N1-piperidine-N5-butyl biguanide; N1-piperidine-N5-hexyl biguanide; N1-pyrrolidine-N5-cyclopentyl biguanide; N1-piperidine-N5-cyclopentyl biguanide; N1-azepane-N5-cyclopentyl biguanide; N1-piperidine-N5-cyclohexyl biguanide; N1-pyrrolidine-N5-cycloheptyl biguanide; N1-piperidine-N5-cycloheptyl biguanide; N1-azepane-N5-cycloheptyl biguanide; N1-pyrrolidine-N5-(pyridine-3-ylmethyl) biguanide; N1-piperidine-N5-(pyridine-3-ylmethyl)biguanide; N1-pyrrolidine-N5-(furan-2-ylmethyl)biguanide; N1-piperidine-N5-(furan-2-ylmethyl) biguanide; N1-piperidine-N5-(thiophene-2-ylmethyl) biguanide; N1-piperidine-N5-(naphthalene-1-yl)methyl biguanide; N1-piperidine-N5-benzyl biguanide; N1-piperidine-N5-(4-methyl)benzyl biguanide; N1-piperidine-N5-(4-methoxy)benzyl biguanide; N1-piperidine-N5-(3-fluoro) benzyl biguanide; N1-piperidine-N5-(4-fluoro)benzyl biguanide; N1-pyrrolidine-N5-(4-chloro)benzyl biguanide; N1-piperidine-N5-(4-chloro)benzyl biguanide; N1-azepane-N5-(4-chloro)benzyl biguanide; N1-pyrrolidine-N5-(4-bromo)benzyl biguanide; N1-piperidine-N5-(4-bromo)benzyl biguanide; N1-morpholine-N5-(3-trifluoromethyl) benzyl biguanide; N1-azetidine-N5-(4-trifluoromethyl) benzyl biguanide; N1-pyrrolidine-N5-(4-trifluoromethyl) benzyl biguanide; N1-piperidine-N5-(4-trifluoromethyl) benzyl biguanide; N1-azetidine-N5-(4-trifluoromethoxy) benzyl biguanide; N1-pyrrolidine-N5-(4-trifluoromethoxy) benzyl biguanide; N1-piperidine-N5-(4-trifluoromethoxy) benzyl biguanide; N1-(4-methyl)piperazine-N5-(4-trifluoromethoxy)benzyl biguanide; N1-piperidine-N5-(4-fluoro-3-trifluoromethyl)benzyl biguanide; N1-piperidine-N5-(4-chloro-3-trifluoromethyl)benzyl biguanide; N1-piperidine-N5-(3-fluoro-4-trifluoromethyl)benzyl biguanide; N1-piperidine-N5-(3-chloro-4-trifluoromethyl)benzyl biguanide; N1-piperidine-N5-(4-fluoro-3-trifluoromethoxy)benzyl biguanide; N1-piperidine-N5-(3-fluoro-4-trifluoromethoxy)benzyl biguanide; N1-piperidine-N5-(3-chloro-4-trifluoromethoxy)benzyl biguanide; N1-piperidine-N5-(2,6-difluoro)benzyl biguanide; N1-piperidine-N5-(3,4-difluoro)benzyl biguanide; N1-piperidine-N5-(2,4-dichloro) benzyl biguanide; N1-pyrrolidine-N5-(3,4-dichloro)benzyl biguanide; N1-piperidine-N5-(3,4-dichloro)benzyl biguanide; N1-piperidine-N5-(thiophene-2-yl)ethyl biguanide; N1-pyrrolidine-N5-(phenethyl)biguanide; N1-piperidine-N5-(phenethyl)biguanide; N1-azepane-N5-(phenethyl)biguanide; N1-azepane-N5-((4-fluoro)phenethyl) biguanide; or N1-azepane-N5-((4-chloro)phenethyl)biguanide.

Meanwhile, a pharmaceutically acceptable salt of the compound of Formula 1 according to the present invention may be an acid addition salt formed using an organic acid or an inorganic acid. For example, the organic acid may include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, dichloroacetic acid, aminooxy acetic acid, benzensulfonic acid, 4-toluenesulfonic acid and methanesulfonic acid, the inorganic acid may include, for example, hydrochloric acid, hydrobromic acid, sulfuric acid, phosphoric acid, nitric acid, carbonic acid and boric acid. For example, the above-described acid addition salt may be prepared by a typical method of preparing a salt, including a) directly mixing the compound of Formula 1 and an acid, b) dissolving one of the compounds and an acid in a solvent or a hydrated solvent and mixing the resulting solution with the other element, or c) dissolving the compound of Formula 1 and an acid in a solvent or hydrated solvent, respectively, and mixing them.

According to one exemplary embodiment, the pharmaceutically acceptable salt of the compound of Formula 1 may be a salt of an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzensulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid and boric acid.

The compound of Formula 1 according to the present invention may be prepared by a number of methods.

According to one exemplary embodiment, there is a method of preparing a compound of Formula 1, which includes reacting a compound of Formula 2 with dicyanoamide in at least one organic solvent to obtain a compound of Formula 3; and reacting the compound of Formula 3 with a compound of Formula 4 in at least one organic solvent to obtain the compound of Formula 1:

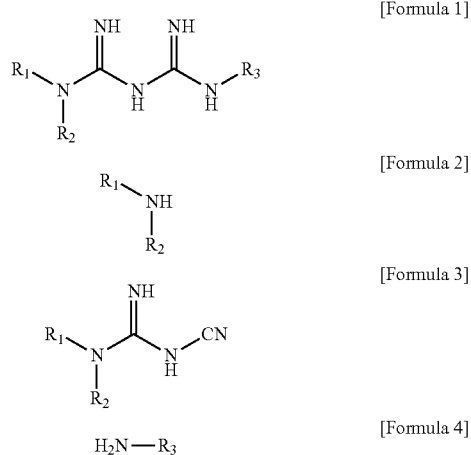

In Formula 1 to 4, $R_1$, $R_2$ and $R_3$ are the same as defined in Formula 1.

For example, the preparation method may be illustrated in the following Scheme 1, and will be described by operations, as follows.

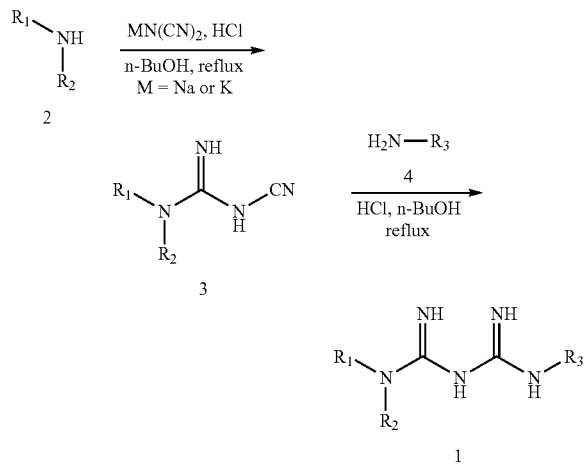

In the method of preparing the compound of Formula 1, the cyanoguanidine compound of Formula 3 used as an intermediate may be obtained by reacting the cyclic amine of Formula 2 with a dicyanoamide such as sodium or potassium dicyanamide in at least one organic solvent, in the presence of an acid. Then, the compound of Formula 1 may be obtained by refluxing the obtained cyanoguanidine compound of Formula 3 with the compound of Formula 4 in water, at least one organic solvent or mixture thereof.

An amount of the dicyanamide used for preparation of the cyanoguanidine compound of Formula 3 is equivalent to approximately 1 to 3 moles with respect to the compound of Formula 2, an amount of the acid (for example, hydrochloric acid, sulfuric acid, nitric acid, hydrobromic acid, 4-toluene sulfonic acid, etc.) is equivalent to approximately 1 to 2 moles with respect to the compound of Formula 2, and methanol, ethanol, propanol, butanol, pentanol, acetonitrile, benzene, toluene, 1,4-dioxane and N,N-dimethylamide, etc. may be used as the organic solvent. The reaction temperature is in the range of 60 to 140° C., and the reaction time is in the range of 3 to 24 hours.

After the cyanoguanidine compound of Formula 3 obtained above is dissolved in water, at least one organic solvent (i.e., methanol, ethanol, propanol, butanol, pentanol, acetonitrile, benzene, toluene, 1,4-dioxane, N,N-dimethylamide, etc.) or mixture thereof, the compound of Formula 4 and the acid (i.e., hydrochloric acid, sulfuric acid, nitric acid, hydrobromic acid, 4-toluene sulfonic acid, etc.) are added, and then stirred under reflux. Here, an amount of the compound of Formula 4 is equivalent to approximately 1 to 2 moles with respect to the compound of Formula 3, and an amount of the acid is equivalent to approximately 1 to 2 moles with respect to the compound of Formula 3. The reaction temperature is in the range of the reflux temperature of the solvent used (i.e., 120 to 140° C. for butanol), and the reaction time is in the range of 6 to 24 hours. When the reaction is completed, the resulting reaction solution is filtered. Thereafter, the pH of the filtrate may then be controlled to approximately 4 to 5 using an acid such as hydrochloric acid. Then, the resulting solution may be concentrated and purified to yield the compound of Formula 1 or a pharmaceutically acceptable salt thereof according to the present invention.

The compound of Formula 1 or the pharmaceutically acceptable salt thereof produced in this way may exhibit anticancer activity including inhibition of cancer metastasis and cancer recurrence, and may also have an effect in lowering blood glucose and lipid concentration by AMPKα activation, even when administered in a small dose compared with conventional drugs, as will be confirmed in the following examples. Therefore, the compound of Formula 1 or the pharmaceutically acceptable salt thereof may be effectively used to treat cancer, diabetes mellitus, obesity, hyperlipemia, hypercholesterolemia, fatty liver, coronary artery disease, osteoporosis, polycystic ovary syndrome and metabolic syndrome.

Accordingly, another aspect of the present invention provides a medicine including the compound of Formula 1 or the pharmaceutically acceptable salt thereof as an active ingredient.

Still another aspect of the present invention provides a pharmaceutical composition for treating or preventing a disease selected from the group consisting of cancer, diabetes mellitus, obesity, hyperlipemia, hypercholesterolemia, fatty liver, coronary artery disease, osteoporosis, polycystic ovary syndrome, metabolic syndrome, muscle pain, myocyte damage and rhabdomyolysis, which includes the compound of Formula 1 or the pharmaceutically acceptable salt thereof as an active ingredient, the use of the compound of Formula 1 or the pharmaceutically acceptable salt thereof for preventing or treating the disease, and a method of preventing or treating the disease including administering a therapeutically effective amount of the compound of Formula 1 or the pharmaceutically acceptable salt thereof to a subject.

According to one exemplary embodiment, the diabetes mellitus may be insulin-independent diabetes mellitus.

The pharmaceutical composition of the present invention includes at least one pharmaceutically acceptable carrier in addition to the active ingredient. As used in this specification, the term "pharmaceutically acceptable carrier" refers to a known pharmaceutically acceptable excipient, which is useful to formulate a pharmaceutically active compound for administration, and is substantially non-toxic and non-sensitive under the conditions it is used. An exact ratio of the excipient is determined by standard pharmaceutical practice, as well as solubility, chemical characteristics and selected route for administration of the active compound.

The pharmaceutical composition of the present invention may be formulated in a form suitable for a desired administration method using a suitable and physiologically acceptable adjuvant such as an excipient, a disintegrating agent, a sweetening agent, a binder, a coating agent, a swelling agent, a lubricating agent, a glossing agent or a flavoring agent.

The pharmaceutical composition may be formulated as a tablet, a capsule, a pill, a granule, a powder, an injection or a liquid, but the present invention is not limited thereto.

The formulation and the pharmaceutically available carrier of the pharmaceutical composition may be properly selected according to the techniques known in the art, and for example, may be selected with reference to the following documents: (Urquhart et al., Lancet, 16:367, 1980); (Lieberman et al., Pharmaceutical Dosage Forms-Disperse Systems, 2nd ed., vol. 3, 1998); (Ansel et al., Pharmaceutical Dosage Forms & Drug Delivery Systems, 7th ed., 2000); (Martindale, The Extra Pharmacopeia, 31st ed.); (Remington's Pharmaceutical Sciences, 16th-20th editions); (The Pharmacological Basis of Therapeutics, Goodman and Gilman, eds., 9th ed., 1996); and (Wilson and Gisvolds' Textbook of Organic Medicinal and Pharmaceutical Chemistry, Delgado and Remers, eds., 10th ed., 1998). Also, principles of formulating a pharmaceutical composition may be described, for example, with reference to the following documents: (Platt, Clin Lab Med, 7:289-99, 1987); (Aulton, Pharmaceutics: The Science of Dosage Form Design, Churchill Livingstone, N.Y., 1988); (Extemporaneous Oral Liquid Dosage Preparations, CSHP, 1998); and ("Drug Dosage", J Kans Med Soc, 70(1):30-32, 1969).

According to one exemplary embodiment, the pharmaceutical composition may be used together with a second drug.

According to the present invention, the term "second drug" refers to another pharmaceutically active ingredient in addition to the biguanide derivative according to the present invention. The compound of Formula 1 or the pharmaceutically acceptable salt thereof according to the present invention may be used to treat a variety of diseases, as described above. As a result, the compound of Formula 1 or the pharmaceutically acceptable salt thereof according to the present invention may be used together with a second drug for effectively treating respective diseases. For example, the second drug may be an anti-hyperglycemic agent, an anti-obesity agent, an anticancer agent, etc.

When the compound of Formula 1 or the pharmaceutically acceptable salt thereof according to the present invention and the second drug are able to be administered in the same manner, the compound of Formula 1 or the pharmaceutically acceptable salt thereof may be formulated together with the second drug to be provided in the form of a composite preparation.

Meanwhile, according to the present invention, the term "subject" refers to a warm-blooded animal, such as a mammal, with a specific condition, disorder or disease. For example, a mammal includes a human, an orangutan, a mouse, a rat, a dog, a cow, a chicken, a pig, a goat, a sheep, etc., but the present invention is not limited thereto.

Also, the term "treating" includes relieving a symptom, temporarily or permanently eliminating causes of the symptom, and preventing or hindering occurrence of the symptom or progression of the above-described condition, disorder or disease, but the present invention is not limited thereto.

An effective amount of the active ingredient of the pharmaceutical composition according to the present invention refers to an amount required to treat a disease. Therefore, the effective amount of the active ingredient may be adjusted according to various factors such as kinds and severity of the disease, kinds and contents of the active ingredient and other ingredients included in the composition, kinds of formulation, age, body weight, general medical conditions, sex and diet of a subject, duration and route of administration, a release rate of the composition, treatment duration, and the number of drugs used together. In the case of an adult, for example, the compound of Formula 1 may be administered in a total dose of 50 to 3,000 mg/kg when administered once to several times a day.

Advantageous Effects of Invention

The N1-cyclic amine-N5-substituted biguanide derivative of Formula 1 according to the present invention is highly effective in inhibiting cancer cell proliferation, cancer metastasis and cancer recurrence, even when administered in a small dose compared with conventional drug, and is also highly effective at lowering blood glucose and lipid concentration. Therefore, the biguanide derivative of Formula 1 according to the present invention may be effectively used to treat diabetes mellitus, obesity, hyperlipemia, hypercholesterolemia, fatty liver, coronary artery disease, osteoporosis, polycystic ovary syndrome and metabolic syndrome, as well as cancer.

MODE FOR THE INVENTION

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Example 1

Synthesis of N1-piperidine cyanoguanidine

Concentrated hydrochloric acid (81.7 ml, 0.940 mol) was added to a solution prepared by dissolving piperidine (92.8 ml, 0.940 mol) in butanol (300 ml) and stirred at 0° C. for 30 minutes. Sodium dicyanamide (92.0 g, 1.03 mol) was added to the mixed solution, and the resulting reaction mixture was stirred for 24 hour under reflux. After the completion of the reaction was confirmed, sodium chloride formed by filtering the reaction mixture was removed, and the filtrate was then concentrated under reduced pressure. Distilled water (100 ml) was added to the concentrate and stirred at room temperature for 1 hour. The formed solid was filtered, and the filter cake was washed with distilled water (2×20 ml). The filter cake was dried under reduced pressure to obtain a white solid target compound (93.3 g, 65%).

$^1$HNMR (600 MHz, DMSO-$d_6$) δ 7.01 (br s, 2H), 3.39 (m, 4H), 1.54 (m, 2H), 1.42 (m, 4H); LC-MS m/z 153.2 [M+1]$^+$; mp 163-165° C.

Example 2

Synthesis of N1-azetidine cyanoguanidine

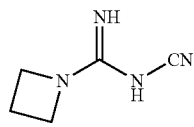

A white solid target compound (1.13 g, 52%) was prepared in the same manner as in Example 1, except that azetidine was used instead of the piperidine which was used in Example 1.

$^1$H NMR (60 MHz, DMSO-$d_6$) δ 6.92 (br s, 2H), 3.91 (t, J=7.8 Hz, 4H), 2.16 (tt, J=7.8, 7.8 Hz, 2H); LC-MS m/z 125.2 [M+1]$^+$; mp 188-189° C.

Example 3

Synthesis of N1-pyrrolidine cyanoguanidine

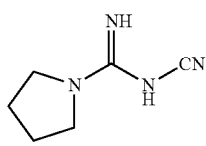

A white solid target compound (24.5 g, 63%) was prepared in the same manner as in Example 1, except that pyrrolidine was used instead of the piperidine which was used in Example 1.

$^1$H NMR (600 MHz, DMSO-$d_6$) δ 6.88 (br s, 2H), 3.24 (m, 4H), 1.80 (m, 4H); LC-MS m/z 139.2 [M+1]$^+$; mp 232-235° C.

Example 4

Synthesis of N1-azepane cyanoguanidine

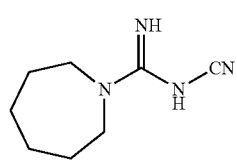

A white solid target compound (10.1 g, 60%) was prepared in the same manner as in Example 1, except that azepane was used instead of the piperidine which was used in Example 1.

$^1$H NMR (600 MHz, DMSO-$d_6$) δ6.88 (br s, 2H), 3.38 (m, 4H), 1.59 (m, 4H), 1.45 (m, 4H); LC-MS m/z 167.2 [M+1]$^+$; mp 168-170° C.

Example 5

Synthesis of N1-morpholine cyanoguanidine

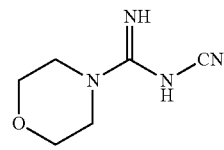 [SMILES: N#CNC(=N)N1CCOCC1]

A white solid target compound (2.04 g, 58%) was prepared in the same manner as in Example 1, except that morpholine was used instead of the piperidine which was used in Example 1.

$^1$H NMR (600 MHz, DMSO-$d_6$) δ 7.12 (br s, 2H), 3.51 (m, 4H), 3.35 (m, 4H); LC-MS m/z 155.1 [M+1]$^+$; mp 171-173° C.

Example 6

Synthesis of N1-(4-methylpiperazine)cyanoguanidine

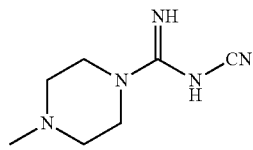

A white solid target compound (1.01 g, 49%) was prepared in the same manner as in Example 1, except that 4-methylpiperazine was used instead of the piperidine which was used in Example 1.

$^1$H NMR (600 MHz, DMSO-$d_6$) δ 7.12 (br s, 2H), 3.39 (t, J=4.8 Hz, 4H), 2.24 (t, J=4.8 Hz, 4H), 2.15 (s, 3H); LC-MS m/z 168.2 [M+1]$^+$; mp 192-194° C.

Example 7

Preparation of N1-piperidine-N5-(3-trifluoromethyl)benzyl biguanide hydrochloride

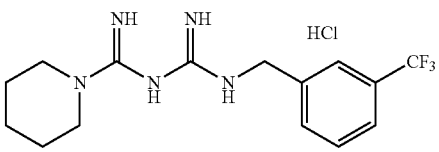 [SMILES: N=C(NCc1cccc(C(F)(F)F)c1)NC(=N)N1CCCCC1 ; Cl]

Concentrated hydrochloric acid (0.14 ml, 1.58 mmol) was added to a solution obtained by dissolving (3-trifluoromethyl)benzyl amine (0.28 mg, 1.58 mmol) in n-butanol (10 ml) and stirred at room temperature for 30 minutes. The compound (0.3 mg, 1.97 mmol) prepared in above step (1-1) was added to the reaction mixture and stirred for 12 hours under reflux. The reaction mixture was concentrated under reduced pressure, the concentrate was then dissolved while adding a 6N hydrochloric acid/methanol solution (3 ml), and a white solid target compound (596 mg, 70%) was obtained using ethyl acetate.

$^1$H NMR (400 MHz, DMSO-d$_6$) d 7.64 (br s, 1H), 7.62-7.55 (m, 4H), 7.40 (br s, 1H), 6.74 (br s, 2H), 4.39 (s, 2H), 3.32 (m, 4H), 1.54 (m, 2H), 1.43 (m, 4H); LCMS m/z 328.3 [M+1]$^+$; mp 259-260° C.

Target compounds of the following Examples 8 to 61 were prepared in the same manner as in Example 7, except that the cyanoguanidine and amine compounds synthesized in Examples 2 to 6, which correspond to the target compounds, were used in stead of the N1-piperidine cyanoguanidine which was synthesized in Example 1 and the (3-trifluoromethyl)benzyl amine which was used in Example 7.

Example 8

N1-piperidine-N5-methyl biguanide hydrochloride

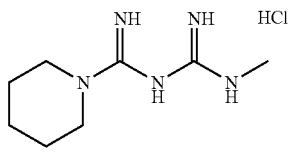

$^1$H NMR (600 MHz, DMSO-d$_6$) d 7.22 (br s, 2H), 3.41 (m, 4H), 2.65 (s, 3H), 1.57 (m, 2H), 1.49 (m, 4H); LCMS m/z 184.3 [M+1]$^+$; mp 211-212° C.

Example 9

N1-piperidine-N5-propyl biguanide hydrochloride

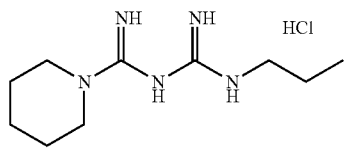

$^1$H NMR (600 MHz, DMSO-d$_6$) d 7.22 (br s, 2H), 3.41 (m, 4H), 2.65 s, 3H), 1.57 (m, 2H), 1.49 (m, 4H); LCMS m/z 184.3 [M+1]$^+$; mp 211-212° C.

Example 10

N1-piperidine-N5-isopropyl biguanide hydrochloride

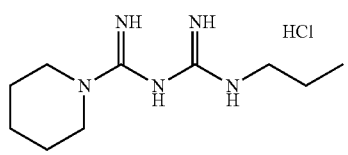

$^1$H NMR (600 MHz, DMSO-d$_6$) d 7.22 (br s, 2H), 3.41 (m, 4H), 2.65 s, 3H), 1.57 (m, 2H), 1.49 (m, 4H); LCMS m/z 184.3 [M+1]$^+$; mp 211-212° C.

Example 11

N1-piperidine-N5-butyl biguanide hydrochloride

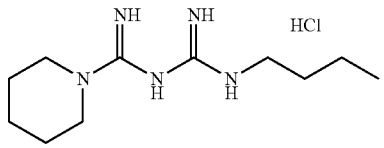 [SMILES: CCCCNC(=N)NC(=N)N1CCCCC1 ; Cl]

$^1$H NMR (600 MHz, DMSO-d$_6$) d 8.18 (br s, 3H), 6.99 (br s, 1H), 3.39 (m, 4H), 2.71 (t, J=7.8 Hz, 2H), 1.56 (m, 4H), 1.42 (m, 4H), 1.32 (m, 2H), 0.87 (m, 3H); LCMS m/z 226.2 [M+H]$^+$; mp 113-114° C.

Example 12

N1-piperidine-N5-hexyl biguanide hydrochloride

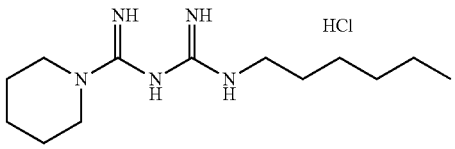 [SMILES: CCCCCCNC(=N)NC(=N)N1CCCCC1 ; Cl]

$^1$H NMR (600 MHz, DMSO-d$_6$) d 7.22 (br s, 2H), 3.41 (m, 4H), 2.65 s, 3H), 1.57 (m, 2H), 1.49 (m, 4H); LCMS m/z 184.3 [M+1]$^+$; mp 211-212° C.

Example 13

N1-pyrrolidine-N5-cyclopentyl biguanide hydrochloride

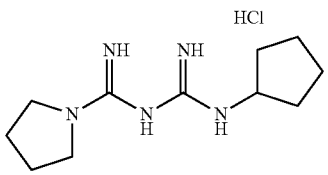 [SMILES: Cl ; N=C(NC(=N)N1CCCC1)NC1CCCC1]

¹H NMR (600 MHz, DMSO-d₆) d 7.36 (br s, 1H), 7.12 (br s, 2H), 6.57 (br s, 1H), 3.89 (m, 1H), 1.85 (m, 8H), 1.63 (m, 2H), 1.48 (m, 6H); LCMS m/z 224.2 [M+H]⁺; mp 200-201° C.

Example 14

N1-piperidine-N5-cyclopentyl biguanide hydrochloride

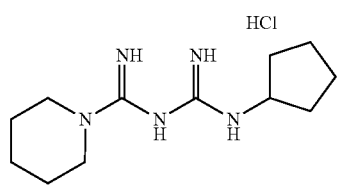 [SMILES: Cl ; N=C(NC(=N)N1CCCCC1)NC1CCCC1]

¹H NMR (600 MHz, DMSO-d₆) d 7.97 (br s, 2H), 3.59 (m, 4H), 3.43 (m, 1H), 1.86 (m, 4H), 1.68 (m, 4H), 1.58-1.45 (m, 6H); LCMS m/z 238.3 [M+H]⁺; mp 154-155° C.

Example 15

N1-azepane-N5-cyclopentyl biguanide hydrochloride

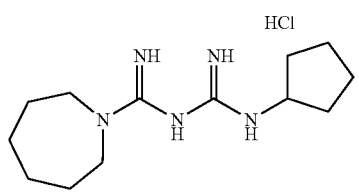 [SMILES: Cl ; N=C(NC(=N)N1CCCCCC1)NC1CCCC1]

¹H NMR (400 MHz, DMSO-d₆) d 7.15 (br s, 1H), 6.94 (br s, 2H), 3.87 (m, 1H), 3.45 (m, 4H), 1.84 (m, 2H), 1.66 (m, 4H), 1.51 (m, 6H); LCMS m/z 252.3 [M+1]⁺; mp 224-225° C.

Example 16

N1-piperidine-N5-cyclohexyl biguanide hydrochloride

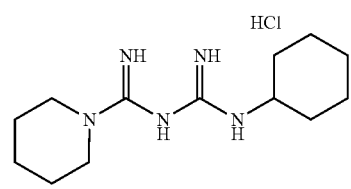 [SMILES: Cl ; N=C(NC(=N)N1CCCCC1)NC1CCCCC1]

¹H NMR (600 MHz, DMSO-d₆) d 7.49 (br s, 2H), 7.13 (br s, 1H), 6.45 (br s, 1H), 3.39 (m, 4H), 2.91 (m, 1H), 1.90 (m, 2H), 1.79 (m, 1H), 1.71 (m, 2H), 1.70-1.65 (m, 6H), 1.27-1.05 (m, 5H); LCMS m/z 252.2 [M+1]⁺; mp 214-215° C.

Example 17

N1-pyrrolidine-N5-cycloheptyl biguanide hydrochloride

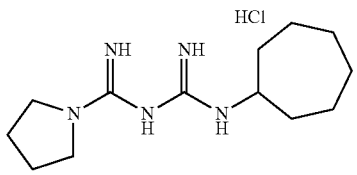 [SMILES: Cl ; N=C(NC(=N)N1CCCC1)NC1CCCCCC1]

¹H NMR (600 MHz, DMSO-d₆) d 7.20 (br s, 1H), 3.61 (m, 1H0, 3.31 (m, 4H), 1.83 (m, 6H), 1.48 (m, 10H); LCMS m/z 252.3 [M+1]⁺; mp 265-266° C.

Example 18

N1-piperidine-N5-cycloheptyl biguanide hydrochloride

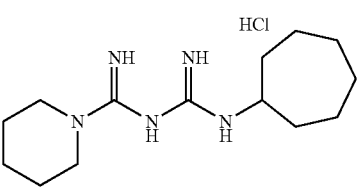 [SMILES: Cl ; N=C(NC(=N)N1CCCCC1)NC1CCCCCC1]

¹H NMR (600 MHz, DMSO-d₆) d 7.97 (br s, 2H), 3.55-3.40 (m, 5H), 1.54 (m, 2H), 1.54-1.38 (m, 16H); LCMS m/z 265.3 [M+1]⁺; mp 237-238° C.

Example 19

N1-azepane-N5-cycloheptyl biguanide hydrochloride

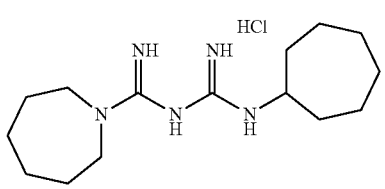

¹H NMR (600 MHz, DMSO-d₆) d 7.23 (br s, 1H), 3.64 (m, 1H), 3.36 (m, 4H), 1.81 (m, 2H), 1.66 (m, 4H), 1.56 (m, 2H), 1.48-1.42 (m, 10H), 1.37 (m, 2H); LCMS m/z 280.3 [M+1]⁺; mp 237-238° C.

Example 20

N1-pyrrolidine-N5-(pyridine-3-ylmethyl)biguanide hydrochloride

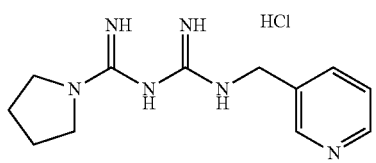 [SMILES: Cl ; N=C(NCc1cccnc1)NC(=N)N1CCCC1]

¹H NMR (600 MHz, DMSO-d₆) d 8.48 (br s, 1H), 8.42 (d, J=6.6 Hz, 1H), 7.68 (d, J=11.4 Hz, 1H), 7.50 (br s, 1H), 7.32 (m, 1H), 7.24 (br s, 1H), 6.91 (br s, 1H), 4.32 (d, J=8.4 Hz, 2H), 3.21 (m, 4H), 1.80 (m, 4H); LCMS m/z 247.2 [M+H]⁺; mp 201-203° C.

Example 21

N1-piperidine-N5-(pyridine-3-ylmethyl)biguanide hydrochloride

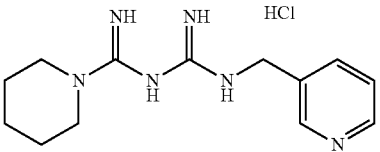 [SMILES: Cl ; N=C(NCc1cccnc1)NC(=N)N1CCCCC1]

¹H NMR (600 MHz, DMSO-d₆) d 8.86 (br s, 2H), 8.81 (d, J=5.4 Hz, 1H), 8.49 (s, 1H), 8.02 (m, 2H), 7.61 (br s, 2H), 4.54 (s, 2H), 3.34 (m, 4H), 1.56 (m, 2H), 1.47 (m, 4H); LCMS m/z 260.1 [M+H]⁺; mp 197-199° C.

Example 22

N1-pyrrolidine-N5-(furan-2-ylmethyl)biguanide hydrochloride

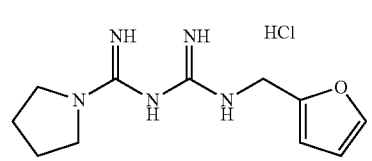 [SMILES: Cl ; N=C(NCc1ccco1)NC(=N)N1CCCC1]

¹H NMR (400 MHz, DMSO-d₆) d 7.59 (d, J=0.8 Hz, 1H), 7.43 (br s, 1H), 7.27 (br s, 2H), 6.70 (br s, 2H), 6.40 (dd, J=2.4, 0.8 Hz, 1H), 6.36 (d, J=2.4 Hz, 1H), 4.30 (d, J=6.0 Hz, 2H), 3.29 (m, 4H), 1.85 (m, 4H); LCMS m/z 236.2 [M+1]⁺; mp 242-243° C.

Example 23

N1-piperidine-N5-(furan-2-ylmethyl)biguanide hydrochloride

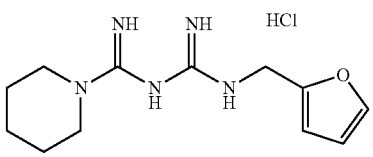 [SMILES: Cl ; N=C(NCc1ccco1)NC(=N)N1CCCCC1]

¹H NMR (400 MHz, DMSO-d₆) d 7.60 (d, J=0.8 Hz, 1H), 7.39 (br s, 2H), 6.64 (br s, 2H), 6.41 (dd, J=1.6, 0.8 Hz, 1H), 6.30 (d, J=1.6 Hz, 1H), 4.29 (d, J=5.2 Hz, 2H), 3.38 (m, 4H), 1.57 (m, 2H), 1.49 (m, 4H); LCMS m/z 250.2 [M+1]⁺; mp 251-252° C.

Example 24

N1-piperidine-N5-(thiophene-2-ylmethyl)biguanide hydrochloride

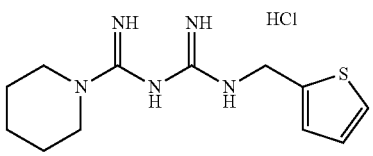

¹H NMR (600 MHz, DMSO-d₆) d 7.57 (br s, 1H), 7.41 (dd, J=5.4, 1.2 Hz, 1H), 7.40 (br s, 2H), 7.01 (d, J=3.0 Hz, 1H), 6.96 (dd, J=5.4, 3.0 Hz, 1H), 6.71 (br s, 2H), 4.47 (d, J=6.0 Hz, 2H), 3.41 (m, 4H), 1.57 (m, 2H), 1.56 (m, 4H); LCMS m/z 266.2 [M+1]⁺; mp 220-221° C.

Example 25

N1-piperidine-N5-(naphthalene-1-yl)methyl biguanide hydrochloride

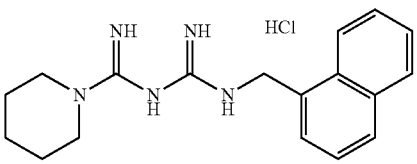 [SMILES: N=C(NCc1cccc2ccccc12)NC(=N)N1CCCCC1 ; Cl]

¹H NMR (600 MHz, DMSO-d₆) d 8.11 (d, J=7.8 Hz, 2H), 7.97 (d, J=7.8 Hz, 2H), 7.87 (d, J=8.4 Hz, 2H), 7.57 (m, 3H), 7.51 (m, 1H), 7.40 (br s, 2H), 6.69 (br s, 2H), 4.78 (d, J=5.4

Hz, 2H), 3.39 (m, 4H), 1.56 (m, 2H), 1.48 (m, 4H); LCMS m/z 210.3 [M+1]⁺; mp 241-242° C.

Example 26

N1-piperidine-N5-benzyl biguanide hydrochloride

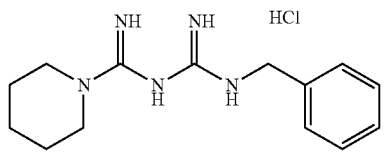 [SMILES: Cl ; N=C(NCc1ccccc1)NC(=N)N1CCCCC1]

$^1$H NMR (600 MHz, DMSO-$d_6$) d 8.70 (br s, 4H), 7.49 (m, 2H), 7.38 (m, 3H), 3.97 (s, 2H), 3.31 (m, 4H), 1.63 (m, 2H), 1.54 (m, 4H); LCMS m/z 260.2 [M+1]⁺; mp 156-158° C.

Example 27

N1-piperidine-N5-(4-methyl)benzyl biguanide hydrochloride

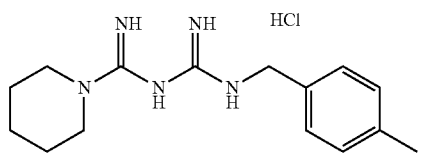 [SMILES: Cl ; Cc1ccc(CNC(=N)NC(=N)N2CCCCC2)cc1]

$^1$H NMR (600 MHz, DMSO-$d_6$) d 7.41 (br s, 1H), 7.27 (br s, 2H), 7.15 (d, J=7.8 Hz, 2H), 7.10 (d, J=7.8 Hz, 2H), 6.62 (br s, 1H), 4.22 (d, J=6.0 Hz, 2H), 3.34 (m, 4H), 2.25 (s, 3H), 1.51 (m, 2H), 1.43 (m, 4H); LCMS m/z 274.2 [M+1]⁺; mp 241-243° C.

Example 28

N1-piperidine-N5-(4-methoxy)benzyl biguanide hydrochloride

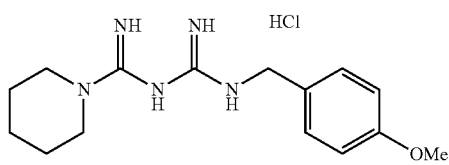 [SMILES: Cl ; COc1ccc(CNC(=N)NC(=N)N2CCCCC2)cc1]

$^1$H NMR (600 MHz, DMSO-$d_6$) d 7.51 (br s, 1H), 7.34 (br s, 2H), 7.24 (d, J=7.8 Hz, 2H), 6.89 (d, J=7.2 Hz, 2H), 6.68 (br s, 1H), 4.23 (d, J=5.4 Hz, 2H), 3.72 (s, 3H), 3.36 (m, 4H), 1.56 (m, 2H), 1.47 (m, 4H); LCMS m/z 290.3 [M+1]⁺; mp 213-214° C.

Example 29

N1-piperidine-N5-(3-fluoro)bezyl biguanide hydrochloride

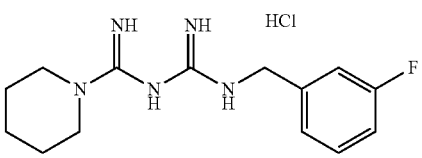 [SMILES: Cl ; N=C(NCc1cccc(F)c1)NC(=N)N1CCCCC1]

$^1$H NMR (400 MHz, DMSO-$d_6$) d 8.55 (br s, 4H), 7.43 (m, 2H), 7.35 (d, J=8.0 Hz, 1H), 7.21 (dd, J=8.8, 8.8 Hz, 1H), 4.04 (s, 2H), 2.97 (m, 4H), 1.67 (m, 4H), 1.57 (m, 2H); LCMS m/z 278.2 [M+1]⁺; mp 171-172° C.

Example 30

N1-piperidine-N5-(4-fluoro)benzyl biguanide hydrochloride

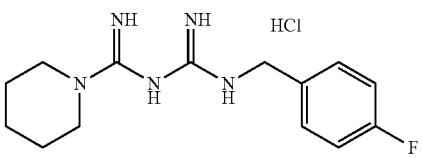 [SMILES: N=C(NCc1ccc(F)cc1)NC(=N)N1CCCCC1 ; Cl]

$^1$H NMR (600 MHz, DMSO-$d_6$) d 7.61 (br s, 1H), 7.37 (br s, 2H), 7.34 (dd, J=7.8, 6.0 Hz, 2H), 7.15 (dd, J=9.0, 7.8 Hz, 2H), 6.72 (br s, 2H), 4.28 (d, J=6.0 Hz, 2H), 3.30 (m, 4H), 1.55 (m, 2H), 1.46 (m, 4H); LCMS m/z 278.2 [M+1]⁺; mp 250-251° C.

Example 31

N1-pyrrolidine-N5-(4-chloro)benzyl biguanide hydrochloride

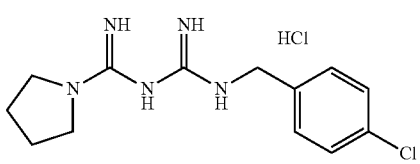 [SMILES: N=C(NCc1ccc(Cl)cc1)NC(=N)N1CCCC1 ; Cl]

¹H NMR (600 MHz, DMSO-d₆) d 7.45 (br s, 1H), 7.42 (m, 2H), 7.38 (m, 2H), 7.24 (br s, 1H), 6.68 (br s, 2H), 4.31 (d, J=9.0 Hz, 2H), 3.25 (m, 4H), 1.87 (m, 4H); LCMS m/z 280.2 [M+1]⁺; mp 250-251° C.

Example 32

N1-piperidine-N5-(4-chloro)benzyl biguanide hydrochloride

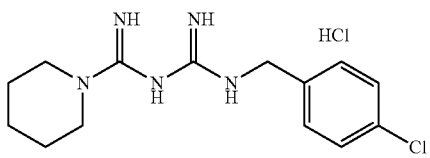 [SMILES: N=C(NCc1ccc(Cl)cc1)NC(=N)N1CCCCC1 ; Cl]

¹H NMR (400 MHz, DMSO-d₆) d 7.40 (d, J=8.0 Hz, 2H), 7.33 (d, J=8.0 Hz, 2H) 4.31 (d, J=4.8 HZ, 2H), 3.34 (m, 4H), 1.55 (m, 2H), 1.47 (m, 4H); LCMS m/z 238.3 [M+1]⁺; mp 169-170° C.

Example 33

N1-azepane-N5-(4-chloro)benzyl biguanide hydrochloride

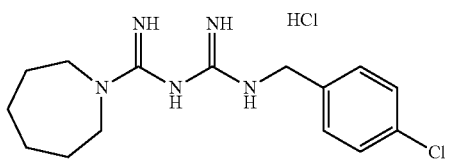 [SMILES: Cl ; N=C(NCc1ccc(Cl)cc1)NC(=N)N1CCCCCC1]

¹H NMR (600 MHz, DMSO-d₆) d 7.40 (d, J=7.8 Hz, 2H), 7.39 (br s, 1H), 7.38-7.32 (m, 7H), 7.25 (d, J=7.8 Hz, 2H), 4.20 (s, 2H), 3.38 (m, 4H), 1.63 (m, 4H), 1.47 (m, 4H); LCMS m/z 308.2 [M+1]⁺; mp 222-223° C.

Example 34

N1-pyrrolidine-N5-(4-bromo)benzyl biguanide hydrochloride

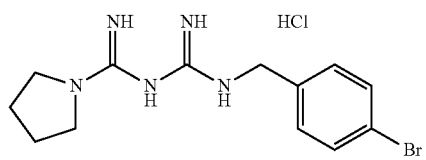 [SMILES: Cl ; N=C(NCc1ccc(Br)cc1)NC(=N)N1CCCC1]

¹H NMR (600 MHz, DMSO-d₆) d 7.91 (br s, 1H), 7.53 (br s, 2H), 7.48 (d, J=8.4 Hz, 2H), 7.23 (d, J=7.8 Hz, 2H), 6.82 (br s, 1H), 4.25 (m, 1H), 3.25 (m, 4H), 1.84 (m, 4H); LCMS m/z 324.2 [M+1]⁺; mp 267-268° C.

Example 35

N1-piperidine-N5-(4-bromo)benzyl biguanide hydrochloride

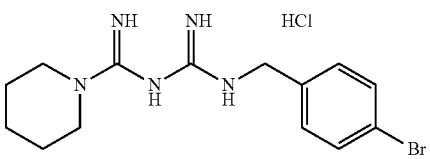 [SMILES: Cl ; N=C(NCc1ccc(Br)cc1)NC(=N)N1CCCCC1]

¹H NMR (600 MHz, DMSO-d₆) d 7.62 (br s, 1H), 7.51 (d, J=7.8 Hz, 2H), 7.38 (br s, 2H), 7.26 (d, J=7.8 Hz, 2H), 6.73 (br s, 2H), 4.27 (d, J=4.8 Hz, 2H), 3.31 (m, 4H), 1.55 (m, 2H), 1.45 (m, 4H); LCMS m/z 339.2 [M+1]⁺; mp 261-262° C.

Example 36

N1-morpholine-N5-(3-trifluoromethyl)benzyl biguanide hydrochloride

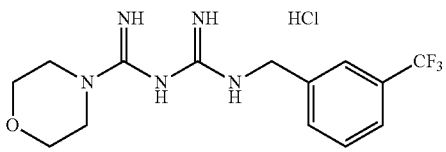 [SMILES: Cl ; N=C(NCc1cccc(C(F)(F)F)c1)NC(=N)N1CCOCC1]

¹H NMR (600 MHz, DMSO-d₆) d 7.89 (br s, 1H), 7.66-7.52 (m, 6H), 6.90 (br s, 1H), 4.40 (d, J=6.0 Hz, 2H), 3.63 (t, J=4.8 Hz, 2H), 3.41 (t, J=4.8 Hz, 2H); LCMS m/z 330.5 [M+1]⁺; mp 211-212° C.

Example 37

N1-azetidine-N5-(4-trifluoromethyl)benzyl biguanide hydrochloride

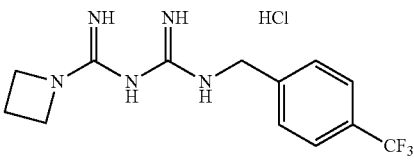 [SMILES: Cl ; N=C(NCc1ccc(C(F)(F)F)cc1)NC(=N)N1CCC1]

¹H NMR (600 MHz, DMSO-d₆) d 7.71 (d, J=7.8 Hz, 2H), 7.70 (br s, 1H), 7.49 (d, J=7.8 Hz, 2H), 7.25 (br s, 2H), 6.86 (br s, 2H), 4.41 (d, J=6.0 Hz, 2H), 3.90 (m, 4H), 2.19 (m, 2H); LCMS m/z 300.0 [M+1]⁺; mp 260-261° C.

Example 38

N1-pyrrolidine-N5-(4-trifluoromethyl)benzyl biguanide hydrochloride

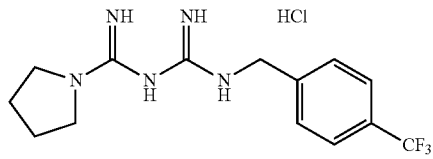 [SMILES: Cl ; N=C(NCc1ccc(C(F)(F)F)cc1)NC(=N)N1CCCC1]

¹H NMR (600 MHz, DMSO-$d_6$) d 7.69 (d, J=7.8 Hz, 2H), 7.66 (br s, 1H), 7.52 (d, J=7.8 Hz, 2H), 7.29 (br s, 2H), 6.77 (br s, 2H), 4.42 (d, J=6.0 Hz, 2H), 3.25 (m, 4H), 1.87 (m, 2H), 1.77 (m, 2H); LCMS m/z 314.1 [M+1]⁺; mp 268-270° C.

Example 39

N1-piperidine-N5-(4-trifluoromethyl)benzyl biguanide hydrochloride

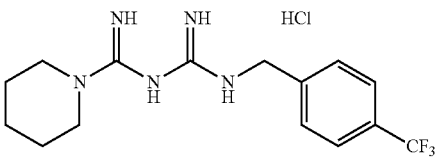 [SMILES: Cl ; N=C(NCc1ccc(C(F)(F)F)cc1)NC(=N)N1CCCCC1]

¹H NMR (600 MHz, DMSO-$d_6$) d 7.69 (d, J=7.8 Hz, 2H), 7.68 (br s, 1H), 7.52 (d, J=7.8 Hz, 2H), 7.39 (br s, 2H), 6.77 (br s, 2H), 4.39 (d, J=5.4 Hz, 2H), 3.31 (m, 4H), 1.53 (m, 2H), 1.41 (m, 4H); LCMS m/z 238.3 [M+1]⁺; mp 267-269° C.

Example 40

N1-azetidine-N5-(4-trifluoromethoxy)benzyl biguanide hydrochloride

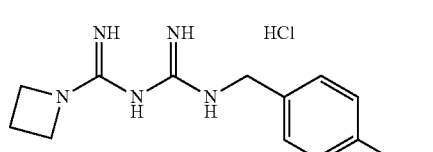

¹H NMR (600 MHz, DMSO-$d_6$) d 7.42 (d, J=6.6 Hz, 2H), 7.35 (m, 6H), 4.35 (d, J=5.4 Hz, 2H), 3.92 (m, 4H), 2.20 (m, 2H); LCMS m/z 316.1 [M+1]⁺; mp 182-184° C.

Example 41

N1-pyrrolidine-N5-(4-trifluoromethoxy)benzyl biguanide hydrochloride

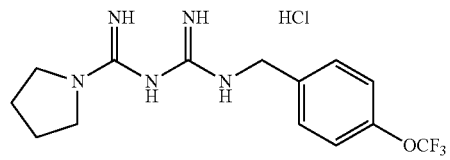 [SMILES: Cl ; N=C(NCc1ccc(OC(F)(F)F)cc1)NC(=N)N1CCCC1]

¹H NMR (600 MHz, DMSO-$d_6$) d 7.56 (br s, 1H), 7.42 (d, J=7.8 Hz, 2H), 7.33 (d, J=7.8 Hz, 2H), 7.28 (br s, 2H), 6.71 (br s, 2H), 4.34 (d, J=6.0 Hz, 2H), 3.28 (m, 4H), 1.87 (m, 2H), 1.77 (m, 2H); LCMS m/z 330.1 [M+1]⁺; mp 242-243° C.

Example 42

N1-piperidine-N5-(4-trifluoromethoxy)benzyl biguanide hydrochloride

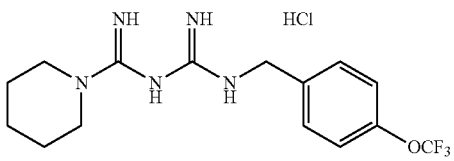 [SMILES: Cl ; N=C(NCc1ccc(OC(F)(F)F)cc1)NC(=N)N1CCCCC1]

¹H NMR (600 MHz, DMSO-$d_6$) d 7.62 (br s, 1H), 7.42 (d, J=8.4 Hz, 2H), 7.37 (br s, 2H), 7.32 (d, J=8.4 Hz, 2H), 6.73 (br s, 2H), 4.33 (d, J=2.4 Hz, 2H), 3.31 (m, 4H), 1.55 (m, 2H), 1.44 (m, 4H); LCMS m/z 344.3 [M+1]⁺; mp 268-269° C.

Example 43

N1-(4-methyl)piperazine-N5-(4-trifluoromethoxy) benzyl biguanide hydrochloride

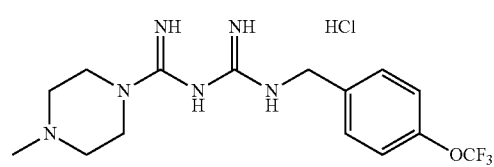 [SMILES: Cl ; CN1CCN(C(=N)NC(=N)NCc2ccc(OC(F)(F)F)cc2)CC1]

¹H NMR (600 MHz, DMSO-$d_6$) d 7.84 (br s, 1H), 7.44 (br s, 2H), 7.42 (d, J=8.4 Hz, 2H), 7.33 (d, J=8.4 Hz, 2H), 6.89 (br s, 2H), 4.33 (d, J=6.0 Hz, 2H), 3.29 (m, 4H), 2.26 (m, 4H), 2.17 (s, 3H); LCMS m/z 259.2 [M+1]⁺; mp 255-257° C.

Example 44

N1-piperidine-N5-(4-fluoro-3-trifluoromethyl)benzyl biguanide hydrochloride

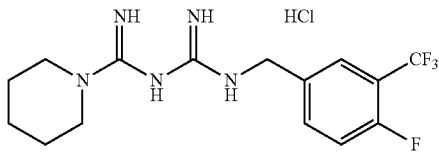 [SMILES: Cl ; N=C(NCc1ccc(F)c(C(F)(F)F)c1)NC(=N)N1CCCCC1]

¹H NMR (600 MHz, DMSO-d₆) d 7.71 (t, J=6.0 Hz, 1H), 7.69 (m, 2H), 7.49 (dd, J=10.8, 8.4 Hz, 1H), 7.43 (br s, 2H), 6.80 (br s, 2H), 4.35 (d, J=6.0 Hz, 2H), 3.31 (m, 4H), 1.54 (m, 2H), 1.43 (m, 4H); LCMS m/z 346.2 [M+1]⁺; mp 232-235° C.

Example 45

N1-piperidine-N5-(4-chloro-3-trifluoromethyl)benzyl biguanide hydrochloride

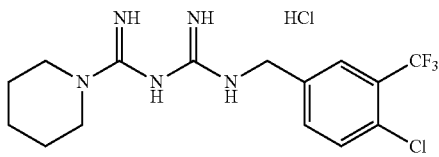 [SMILES: Cl ; N=C(NCc1ccc(Cl)c(C(F)(F)F)c1)NC(=N)N1CCCCC1]

¹H NMR (600 MHz, DMSO-d₆) d 7.78 (m, 2H), 7.69 (d, J=7.8 Hz, 2H), 7.62 (d, J=7.8 Hz, 1H), 7.44 (br s, 2H), 6.81 (br s, 2H), 4.36 (d, J=6.0 Hz, 2H), 3.30 (m, 4H), 1.54 (m, 2H), 1.43 (m, 4H); LCMS m/z 362.0 [M+1]⁺; mp 259-261° C.

Example 46

N1-piperidine-N5-(3-fluoro-4-trifluoromethyl)benzyl biguanide hydrochloride

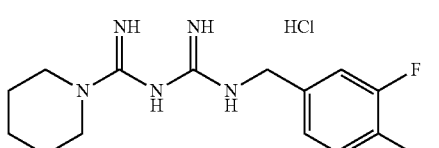

¹H NMR (600 MHz, DMSO-d₆) d 7.74 (m, 2H), 7.45 (br s, 2H), 7.42 (d, J=12.0 Hz, 1H), 7.33 (d, J=7.8 Hz, 1H), 6.81 (br s, 2H), 4.39 (d, J=6.0 Hz, 2H), 3.33 (m, 4H), 1.54 (m, 2H), 1.42 (m, 4H); LCMS m/z 346.1 [M+1]⁺; mp 264-266° C.

Example 47

N1-piperidine-N5-(3-chloro-4-trifluoromethyl)benzyl biguanide hydrochloride

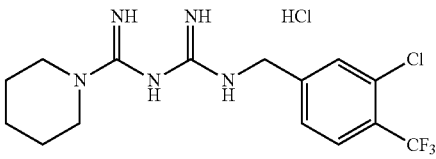 [SMILES: Cl ; N=C(NCc1ccc(C(F)(F)F)c(Cl)c1)NC(=N)N1CCCCC1]

¹H NMR (600 MHz, DMSO-d₆) d 7.82 (d, J=8.4 Hz, 1H), 7.77 (t, J=6.0 Hz, 1H), 7.63 (s, 1H), 7.47 (d, J=8.4 Hz, 1H), 7.46 (br s, 2H), 6.82 (br s, 2H), 4.38 (d, J=6.0 Hz, 2H), 3.29 (m, 4H), 1.53 (m, 2H), 1.42 (m, 4H); LCMS m/z 362.0 [M+1]⁺; mp 254-256° C.

Example 48

N1-piperidine-N5-(4-fluoro-3-trifluoromethoxy) benzyl biguanide hydrochloride

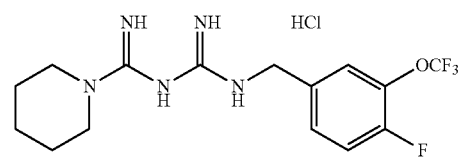 [SMILES: Cl ; N=C(NCc1ccc(F)c(OC(F)(F)F)c1)NC(=N)N1CCCCC1]

¹H NMR (600 MHz, DMSO-d₆) d 7.71 (t, J=6.0 Hz, 1H), 7.49-7.39 (m, 5H), 6.79 (br s, 2H), 4.32 (d, J=6.0 Hz, 2H), 3.31 (m, 4H), 1.54 (m, 2H), 1.43 (m, 4H); LCMS m/z 362.2 [M+1]⁺; mp 233-235° C.

Example 49

N1-piperidine-N5-(3-fluoro-4-trifluoromethoxy) benzyl biguanide hydrochloride

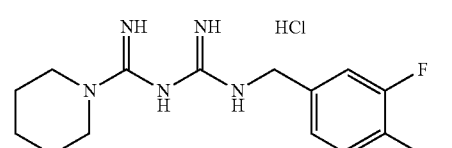

¹H NMR (600 MHz, DMSO-d₆) d 7.69 (br s, 1H), 7.53 (dd, J=8.4, 7.8 Hz, 1H), 7.43 (br s, 2H), 7.42 (d, J=7.8 Hz, 1H), 7.24 (d, J=8.4 Hz, 1H), 6.77 (br s, 2H), 4.33 (d, J=5.4 Hz, 2H), 3.31 (m, 4H), 1.54 (m, 2H), 1.43 (m, 4H); LCMS m/z 362.2 [M+1]⁺; mp 266-268° C.

Example 50

N1-piperidine-N5-(3-chloro-4-trifluoromethoxy) benzyl biguanide hydrochloride

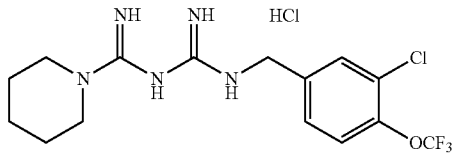 [SMILES: N=C(NCc1ccc(OC(F)(F)F)c(Cl)c1)NC(=N)N1CCCCC1 ; Cl]

¹H NMR (600 MHz, DMSO-d₆) d 7.74 (t, J=6.0 Hz, 1H), 7.60 (s, 1H), 7.53 (d, J=9.0 Hz, 1H), 7.43 (br s, 2H), 7.40 (d, J=9.0 Hz, 1H), 6.79 (br s, 2H), 4.33 (d, J=6.0 Hz, 2H), 3.31 (m, 4H), 1.54 (m, 2H), 1.43 (m, 4H); LCMS m/z 378.2 [M+1]⁺; mp 240-241° C.

Example 51

N1-piperidine-N5-(2,6-difluoro)benzyl biguanide hydrochloride

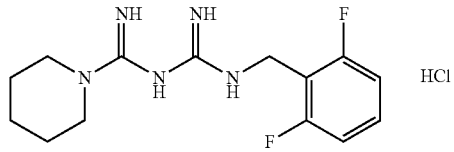 [SMILES: N=C(NCc1c(F)cccc1F)NC(=N)N1CCCCC1 ; Cl]

¹H NMR (600 MHz, DMSO-d₆) d 7.56 (t, J=5.4 Hz, 1H), 7.38 (m, 2H), 7.09 (dd, J=7.8, 7.8 Hz, 2H), 6.67 (br s, 2H), 4.36 (d, J=5.4 Hz, 2H), 3.36 (m, 4H), 1.56 (m, 2H), 1.47 (m, 4H); LCMS m/z 296.3 [M+1]⁺; mp 229-232° C.

Example 52

N1-piperidine-N5-(3,4-difluoro)benzyl biguanide hydrochloride

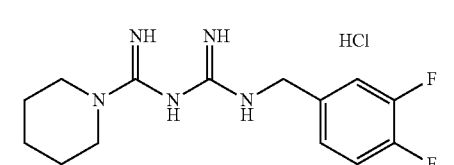

¹H NMR (600 MHz, DMSO-d₆) d 7.67 (m, 1H), 7.41-7.34 (m, 3H), 7.15 (m, 1H), 6.77 (br s, 2H), 4.30 (d, J=6.0 Hz, 2H), 3.34 (m, 4H), 1.55 (m, 2H), 1.46 (m, 4H); LCMS m/z 296.3 [M+1]⁺; mp 230-232° C.

Example 53

N1-piperidine-N5-(2,4-dichloro)benzyl biguanide hydrochloride

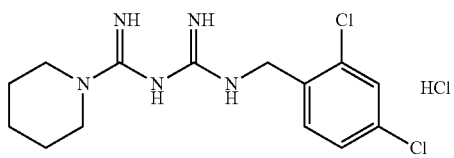 [SMILES: N=C(NCc1ccc(Cl)cc1Cl)NC(=N)N1CCCCC1 ; Cl]

¹H NMR (600 MHz, DMSO-d₆) d 7.60 (br s, 1H), 7.42 (m, 4H), 6.76 (br s, 2H), 4.34 (d, J=6.0 Hz, 2H), 3.31 (m, 4H), 1.55 (m, 2H), 1.45 (m, 4H); LCMS m/z 328.0 [M+1]⁺; mp 240-241° C.

Example 54

N1-pyrrolidine-N5-(3,4-dichloro)benzyl biguanide hydrochloride

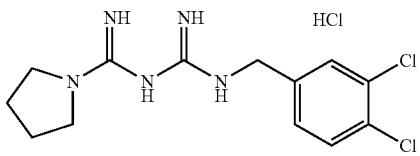 [SMILES: N=C(NCc1ccc(Cl)c(Cl)c1)NC(=N)N1CCCC1 ; Cl]

¹H NMR (600 MHz, DMSO-d₆) d 7.55 (d, J=8.4 Hz, 1H), 7.52 (m, 2H), 7.26 (dd, J=8.4, 1.2 Hz, 1H), 7.23 (br s, 2H), 4.28 (d, J=6.0 Hz, 2H), 3.21 (m, 4H), 1.80 (m, 4H); LCMS m/z 314.1 [M+1]⁺; mp 219-221° C.

Example 55

N1-piperidine-N5-(3,4-dichloro)benzyl biguanide hydrochloride

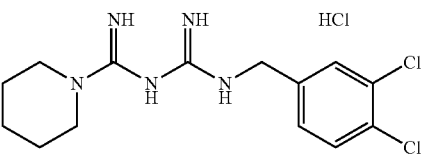 [SMILES: Cl ; N=C(NCc1ccc(Cl)c(Cl)c1)NC(=N)N1CCCCC1]

¹H NMR (600 MHz, DMSO-d₆) d 7.66 (br s, 1H), 7.59 (d, J=7.8 Hz, 1H), 7.55 (s, 1H), 7.40 (br s, 1H), 7.30 (dd, J=7.8, 1.8 Hz, 1H), 6.76 (br s, 2H), 4.30 (d, J=3.6 Hz, 2H), 3.32 (m, 4H), 1.55 (m, 2H), 1.45 (m, 4H); LCMS m/z 328.0 [M+1]⁺; mp 242-244° C.

Example 56

N1-piperidine-N5-(thiophene-2-yl)ethyl biguanide hydrochloride

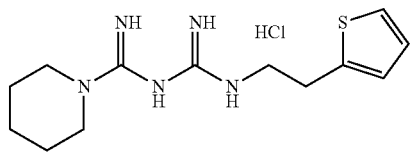 [SMILES: N=C(NCCc1cccs1)NC(=N)N1CCCCC1 ; Cl]

¹H NMR (600 MHz, DMSO-d₆) d 8.51 (br s, 2H), 7.42 (m, 1H), 7.12 (br s, 1H), 6.98 (m, 2H), 6.93 (br s, 1H), 3.42 (m, 2H), 3.15 (m, 4H), 3.03 (t, J=5.4 Hz, 2H), 1.55 (m, 6H); LCMS 280.2 m/z [M+1]⁺; mp 176-178° C.

Example 57

N1-pyrrolidine-N5-(phenethyl)biguanide hydrochloride

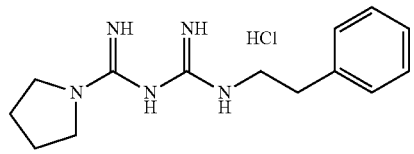 [SMILES: N=C(NCCc1ccccc1)NC(=N)N1CCCC1 ; Cl]

¹H NMR (600 MHz, DMSO-d₆) d 7.30 (m, 2H), 7.22 (m, 3H), 3.25-3.27 (m, 6H), 2.77 (t, J=1.8 Hz, 2H), 1.89 (m, 4H); LCMS m/z 260.2 [M+H]⁺; mp 213-215° C.

Example 58

N1-piperidine-N5-(phenethyl)biguanide hydrochloride

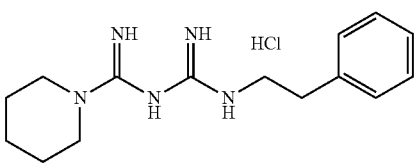 [SMILES: N=C(NCCc1ccccc1)NC(=N)N1CCCCC1 ; Cl]

¹H NMR (600 MHz, DMSO-d₆) d 7.32-7.21 (m, 7H), 3.41 (m, 4H), 3.36 (m, 2H), 2.74 (m, 2H), 1.58 (m, 2H), 1.53 (m, 4H); LCMS m/z 274.2 [M+H]⁺; mp 235-237° C.

Example 59

N1-azepane-N5-(phenethyl)biguanide hydrochloride

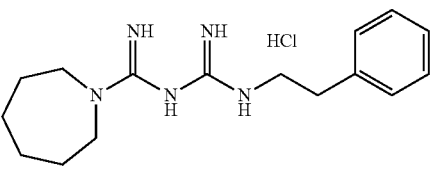 [SMILES: N=C(NCCc1ccccc1)NC(=N)N1CCCCCC1 ; Cl]

¹H NMR (600 MHz, DMSO-d₆) d 7.31-7.21 (m, 8H), 3.46 (m, 4H), 3.37 (m, 2H), 2.79 (m, 2H), 1.68 (m, 4H), 1.52 (m, 4H); LCMS m/z 288.2 [M+1]⁺; mp 211-213° C.

Example 60

N1-azepane-N5-((4-fluoro)phenethyl)biguanide hydrochloride

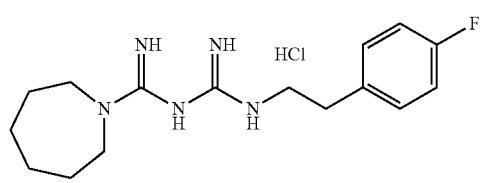 [SMILES: N=C(NCCc1ccc(F)cc1)NC(=N)N1CCCCCC1 ; Cl]

¹H NMR (400 MHz, DMSO-d₆) d 7.27 (m, 3H), 7.12 (dd, J=8.8, 8.8 Hz, 2H), 3.43 (m, 4H), 3.32 (m, 2H), 2.76 (m, 2H), 1.66 (m, 4H), 1.51 (m, 4H); LCMS m/z 306.3 [M+1]⁺; mp 211-212° C.

Example 61

N1-azepane-N5-((4-chloro)phenethyl)biguanide hydrochloride

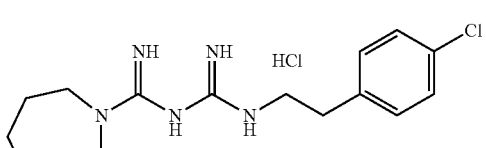

¹H NMR (400 MHz, DMSO-d₆) d 7.36 (d, J=8.0 Hz, 2H), 7.35 (br s, 1H), 7.25 (d, J=8.0 Hz, 2H), 7.18 (br s, 1H), 7.06 (br s, 1H), 3.40 (m, 4H), 3.30 (m, 2H), 2.75 (t, J=7.2 Hz, 2H), 1.63 (m, 4H), 1.50 (m, 4H); LCMS m/z 322.2 [M+1]⁺; mp 181-183° C.

EXPERIMENTAL EXAMPLES

The compounds synthesized by the methods described in the examples of the present invention were evaluated for effects of AMPK-activation and inhibition of cancer cell proliferation according to methods described in the following Experimental Examples.

Experimental Example 1

Measurement of AMPK-Activation Effect

MCF7 cells derived from human breast cancer cells (commercially available from the Korean Cell Line Bank) were used, and the AMPK (5'-AMP-activated protein kinase alpha)-activation effect of the biguanide derivative was confirmed using an AMPKα immunoassay kit (Invitrogen, Catalog No. KH00651).

MCF7 cells were cultured in a DMEM medium supplemented with 10% fetal bovine serum. Thereafter, the cultured MCF7 cells were put into a 6-well plate with approximately $5 \times 10^5$ cells per well and cultured in an incubator supplied with 5% $CO_2$. Culture media were treated with the derivatives synthesized in the examples at contents of 5, 10 and 50 µM, and then cultured for 24 hours. Metformin hydrochloride was used as the control, and the culture media were treated with 0.05, 0.5, 1, 2, 5 and 10 mM metformin hydrochloride, and then tested in the same manner as described in the derivatives synthesized in the examples. Subsequently, the cells were lysed according to a method presented in the operation manual of the AMPKα immunoassay kit, and 20 µg of a cell lysate was then yielded through protein assay. Thereafter, the AMPK activation effect was obtained by determining the degree of phosphorylation of $172^{nd}$ threonine residue (Thr172) of the AMPKα from the cell lysate according to the method presented in the operation manual of the AMPKα immunoassay kit. The degree of AMPK activation by the biguanide derivatives was exhibited as the degree of AMPKα phosphorylation in cells cultured in the presence of the compounds synthesized in the examples with respect to the degree of AMPKα phosphorylation in cells cultured without the treatment of the biguanide derivatives. A curve graph showing AMPK activation according to the concentration of the treated compounds was plotted based on the obtained AMPKα activation results, the concentration (activation concentration 150, AC150) value of the compound whose AMPK activation reached 150% was calculated using a GraphPad Prism 5.0 program, and the degrees of AMPK activation were obtained when concentrations of the treated biguanide derivatives were 10 µM and 50 µM and the metformin hydrochloride was 50 µM.

The results are listed in the following Table 1.

TABLE 1

| Example | AMPK activation effect | | |
|---|---|---|---|
| | AC150 (uM) | 10 uM (%) | 50 uM (%) |
| Metformin hydrochloride | 188.3 | | 130 |
| 7 | 1.0 | 582 | 677 |
| 8 | 9.0 | 139 | 500 |
| 11 | >50 | | 130 |
| 13 | 11.9 | 131 | 375 |
| 14 | 38.3 | 114 | 157 |
| 15 | 7.0 | 174 | 291 |
| 16 | 8.0 | 167 | 486 |
| 17 | 7.9 | 149 | 612 |
| 18 | 2.2 | 304 | 719 |
| 19 | 5.6 | 213 | 325 |
| 20 | >50 | 71 | 89 |
| 22 | 18.3 | 101 | 293 |
| 23 | 15.8 | 112 | 298 |
| 24 | >50 | 64 | 112 |

TABLE 1-continued

| Example | AMPK activation effect | | |
|---|---|---|---|
| | AC150 (uM) | 10 uM (%) | 50 uM (%) |
| 25 | 8.0 | | 428 |
| 27 | 2.3 | 435 | 947 |
| 28 | 3.9 | 258 | 628 |
| 29 | >50 | | 131 |
| 30 | 13.1 | 143 | 278 |
| 31 | 2.3 | 304 | 776 |
| 33 | 1.2 | | 443 |
| 34 | 42.4 | 467 | 639 |
| 35 | 1.1 | 140 | 150 |
| 36 | >50 | 516 | 656 |
| 37 | 24.2 | 100 | 107 |
| 38 | 1.4 | 116 | 213 |
| 39 | 0.9 | 476 | 615 |
| 40 | 3.9 | 673 | 1076 |
| 41 | 0.9 | 242 | 698 |
| 42 | 0.8 | 472 | 554 |
| 43 | 6.4 | 669 | 854 |
| 44 | 10.3 | 180 | 383 |
| 45 | 1.7 | 162 | 232 |
| 46 | 1.1 | 331 | 389 |
| 47 | 4.4 | 433 | 384 |
| 48 | 18.2 | 244 | |
| 49 | 0.8 | 158 | 147 |
| 50 | 8.8 | 259 | |
| 51 | 2.1 | 179 | |
| 52 | 3.8 | 327 | 703 |
| 53 | 3.5 | 238 | 831 |
| 54 | 0.8 | 315 | |
| 55 | 0.9 | 443 | 830 |
| 56 | 9.0 | 612 | |
| 57 | 8.1 | | 391 |
| 58 | 6.4 | 167 | 388 |
| 59 | 0.7 | 194 | 373 |
| 60 | 0.7 | 744 | 721 |
| 61 | 0.5 | 1130 | |

Experimental Example 2

Measurement of Effect of Inhibiting Cancer Cell Proliferation

HCT116 cells derived from human colorectal cancer (commercially available from the Korean Cell Line Bank) were used, and the effect of inhibiting cancer cell proliferation of the biguanide derivative was confirmed by measuring the concentration value (cell growth inhibition concentration, GIC50) at which cell growth was inhibited by 50% using a 3-(4,5-dimethylthiazol-2-yl)-2,5-ditetrazolium bromide (MTT) reagent.

First, HCT116 cells were put on a 96-well plate and cultured in a DMEM medium containing 10% fetal bovine serum for 16 hours so that the cellcount in each well was approximately 5,000. Subsequently, to obtain the GIC50 value of each compound, culture media were treated with 100 µM, 25 µM, 6.25 µM, 1.56 µM or 0.39 µM of the compound, and then cultured for 48 hours. At this time, some of the compounds were treated with 200 µM instead of 100 µM. Metformin hydrochloride was used as the control, and the culture media were treated with 25, 12.5, 2.5, 0.5, 0.1 mM metformin hydrochloride, and then tested in the same manner as described in the derivatives synthesized in the examples. In order to determine whether the cells survived after treatment with the compound, MTT was added to the culture media which were then cultured for another 3 hours. Formed formazane crystals were dissolved using dimethyl sulfoxide (DMSO), and the absorbance of the resulting solution was measured at 560 nm. After the 48-hours culture, the ratio of the cell count cultured on a well plate not treated with the compound to the living cell count on a well plate treated with the compounds synthesized in the examples was indicated as cell viability (%) according to each treated concentration. A cell viability curve graph was plotted and the concentration (GIC50) value of the compound at which the growth was inhibited by 50% was calculated to confirm the effect of inhibition of cancer cell proliferation. Also, the cell growth viability (%) when the concentration of the treated biguanide derivative and the metformin hydrochloride as the control were 100 uM was shown.

The results of measuring effects on cancer cell growth inhibition are listed in the following Table 2.

TABLE 2

| | Effect of inhibition on cancer cell growth | |
|---|---|---|
| Example | GI50 (uM) | Cell Growth Inhibition (%) at 100 uM |
| Metformin hydrochloride | 2846 | 1.8 |
| 7 | 17.2 | 97.4 |
| 8 | 88.6 | 50.5 |
| 11 | >100 | 42.7 |
| 13 | >100 | 41.9 |
| 14 | >100 | 30.4 |
| 15 | >100 | 27.9 |
| 16 | >100 | 49.1 |
| 17 | 41.0 | 60.8 |
| 18 | 23.1 | 64.3 |
| 19 | 35.7 | 94.7 |
| 20 | >100 | 9.2 |
| 22 | >100 | 43.9 |
| 23 | >100 | 39.5 |
| 24 | 93.2 | 51.7 |
| 25 | 28.0 | 96.6 |
| 27 | 70.5 | 64.9 |
| 28 | >100 | 28.3 |
| 30 | >100 | 47.0 |
| 31 | 17.6 | 65.9 |
| 33 | 4.9 | 25.3 |
| 34 | 92.8 | 97.3 |
| 35 | 23.2 | 53.8 |
| 36 | >100 | 97.2 |
| 37 | 39.3 | 23.5 |
| 38 | 32.4 | 61.6 |
| 39 | 16.2 | 78.9 |
| 40 | 36.9 | 97.8 |
| 41 | 25.6 | 97.4 |
| 42 | 16.2 | 96.8 |
| 43 | >100 | 97.7 |
| 44 | 15.2 | 32.6 |
| 45 | 8.2 | 96.9 |
| 46 | 21.3 | 100.6 |
| 47 | 7.4 | 100.4 |
| 48 | 13.4 | 96.4 |
| 49 | 9.2 | 97.0 |
| 50 | 5.7 | 97.0 |
| 51 | >100 | 96.8 |
| 52 | 76.4 | 46.5 |
| 53 | 9.1 | 63.7 |
| 54 | 21.1 | 98.0 |
| 55 | 10.3 | 97.7 |
| 56 | ND | 97.6 |
| 57 | >200 | 23.2 (at 200 uM) |
| 58 | 43.2 | 32.3 |
| 59 | 21.9 | 56.6 |
| 60 | 22.4 | 73.7 |
| 61 | 19.8 | 94.3 |

The invention claimed is:

1. A compound of Formula 1 or a pharmaceutically acceptable salt thereof:

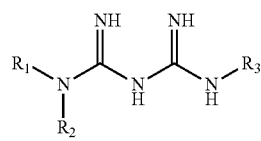

[Formula 1]

wherein $R_1$ and $R_2$ are taken together with nitrogen to which they are attached to form 3- to 8-membered heterocycloalkyl, $R_3$ is $C_{4-7}$ cycloalkyl; or $C_{1-12}$ alkyl unsubstituted or substituted with $C_{3-12}$ aryl or $C_{3-12}$ heteroaryl, wherein $C_{4-7}$ cycloalkyl, 3- to 8-membered heterocycloalkyl, $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

2. The compound of Formula 1 or the pharmaceutically acceptable salt thereof of claim 1, wherein $R_1$ and $R_2$ are taken together with nitrogen to which they are attached to form 4- to 7-membered heterocycloalkyl, $R_3$ is $C_{4-7}$ cycloalkyl; or $C_{1-12}$ alkyl unsubstituted or substituted with $C_{3-12}$ aryl or $C_{3-12}$ heteroaryl, wherein $C_{4-7}$ cycloalkyl, 4- to 7-membered heterocycloalkyl, $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

3. The compound of Formula 1 or the pharmaceutically acceptable salt thereof of claim 1, wherein $C_{3-12}$ aryl is a phenyl or naphthalenyl, $C_{3-12}$ heteroaryl is a furanyl, thiophenyl, pyridinyl, pyrrolyl, imidazolyl or pyrimidinyl, $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

4. The compound of Formula 1 or the pharmaceutically acceptable salt thereof of claim 1, wherein $R_1$ and $R_2$ are taken together with nitrogen to which they are attached to form 3- to 8-membered heterocycloalkyl selected from the group consisting of an azetidinyl, pyrrolidinyl, piperidinyl, morpholinyl, piperazinyl, azepanyl and aziridinyl, $R_3$ is $C_{4-7}$ cycloalkyl; or $C_{1-12}$ alkyl unsubstituted or substituted with $C_{3-12}$ aryl or $C_{3-12}$ heteroaryl, wherein $C_{4-7}$ cycloalkyl, 3- to 8-membered heterocycloalkyl, $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

5. The compound of Formula 1 or the pharmaceutically acceptable salt thereof of claim 1, wherein $R_1$ and $R_2$ are taken together with nitrogen to which they are attached to form 3- to 8-membered heterocycloalkyl selected from the group consisting of an azetidinyl, pyrrolidinyl, piperidinyl, morpholinyl, piperazinyl, azepanyl and aziridinyl, $R_3$ is $C_{4-7}$ cycloalkyl; or $C_{1-12}$ alkyl unsubstituted or substituted with $C_{3-12}$ aryl or $C_{3-12}$ heteroaryl which is selected from the group consisting of a phenyl, naphthalenyl, furanyl, thiophenyl, pyridinyl, pyrrolyl and imidazolyl,
wherein 3- to 8-membered heterocycloalkyl, $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

6. The compound of Formula 1 or the pharmaceutically acceptable salt thereof of claim 1,
wherein $R_1$ and $R_2$ are taken together with nitrogen to which they are attached to form 4- to 7-membered heterocycloalkyl selected from the group consisting of an azetidinyl, pyrrolidinyl, piperidinyl, morpholinyl, piperazinyl and azepanyl,
$R_3$ is $C_{4-7}$ cycloalkyl; or $C_{1-12}$ alkyl unsubstituted or substituted with $C_{3-12}$ aryl or $C_{3-12}$ heteroaryl which is selected from the group consisting of a phenyl, naphthalenyl, furanyl, thiophenyl and pyridinyl,
wherein 4- to 7-membered heterocycloalkyl, $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

7. The compound of Formula 1 or the pharmaceutically acceptable salt thereof of claim 1,
wherein $R_1$ and $R_2$ are taken together with nitrogen to which they are attached to form 4- to 7-membered heterocycloalkyl selected from the group consisting of an azetidinyl, pyrrolidinyl, piperidinyl, morpholinyl, piperazinyl and azepanyl, wherein piperazinyl is substituted with $C_{1-6}$ alkyl,
$R_3$ is $C_{4-7}$ cycloalkyl; or $C_{1-6}$ alkyl that is unsubstituted or substituted with $C_{3-12}$ aryl or $C_{3-12}$ heteroaryl which is selected from the group consisting of a phenyl, naphthalenyl, furanyl, thiophenyl and pyridinyl, wherein $C_{3-12}$ aryl or $C_{3-12}$ heteroaryl is unsubstituted or substituted with at least one non-hydrogen substituent selected from the group consisting of halogen, $C_{1-4}$ alkyl, $C_{1-4}$ alkoxy, haloalkyl and haloalkoxy.

8. The compound of Formula 1 or the pharmaceutically acceptable salt thereof of claim 1, wherein the compound of Formula 1 is
N1-piperidine-N5-(3-trifluoromethyl)benzyl biguanide;
N1-piperidine-N5-methyl biguanide;
N1-piperidine-N5-propyl biguanide;
N1-piperidine-N5-isopropyl biguanide;
N1-piperidine-N5-butyl biguanide;
N1-piperidine-N5-hexyl biguanide;
N1-pyrrolidine-N5-cyclopentyl biguanide;
N1-piperidine-N5-cyclopentyl biguanide;
N1-azepane-N5-cyclopentyl biguanide;
N1-piperidine-N5-cyclohexyl biguanide;
N1-pyrrolidine-N5-cycloheptyl biguanide;
N1-piperidine-N5-cycloheptyl biguanide;
N1-azepane-N5-cycloheptyl biguanide;
N1-pyrrolidine-N5-(pyridine-3-ylmethyl) biguanide;
N1-piperidine-N5-(pyridine-3-ylmethyl) biguanide;
N1-pyrrolidine-N5-(furan-2-ylmethyl) biguanide;
N1-piperidine-N5-(furan-2-ylmethyl) biguanide;
N1-piperidine-N5-(thiophene-2-ylmethyl) biguanide;
N1-piperidine-N5-(naphthalene-1-yl)methyl biguanide;
N1-piperidine-N5-benzyl biguanide;
N1-piperidine-N5-(4-methyl)benzyl biguanide;
N1-piperidine-N5-(4-methoxy)benzyl biguanide;
N1-piperidine-N5-(3-fluoro)benzyl biguanide;
N1-piperidine-N5-(4-fluoro)benzyl biguanide;
N1-pyrrolidine-N5-(4-chloro)benzyl biguanide;
N1-piperidine-N5-(4-chloro)benzyl biguanide;
N1-azepane-N5-(4-chloro)benzyl biguanide;
N1-pyrrolidine-N5-(4-bromo)benzyl biguanide;
N1-piperidine-N5-(4-bromo)benzyl biguanide;
N1-morpholine-N5-(3-trifluoromethyl)benzyl biguanide;
N1-azetidine-N5-(4-trifluoromethyl)benzyl biguanide;
N1-pyrrolidine-N5-(4-trifluoromethyl)benzyl biguanide;
N1-piperidine-N5-(4-trifluoromethyl)benzyl biguanide;
N1-azetidine-N5-(4-trifluoromethoxy)benzyl biguanide;
N1-pyrrolidine-N5-(4-trifluoromethoxy)benzyl biguanide;
N1-piperidine-N5-(4-trifluoromethoxy)benzyl biguanide;
N1-(4-methyl)piperazine-N5-(4-trifluoromethoxy)benzyl biguanide;
N1-piperidine-N5-(4-fluoro-3-trifluoromethyl)benzyl biguanide;
N1-piperidine-N5-(4-chloro-3-trifluoromethyl)benzyl biguanide;
N1-piperidine-N5-(3-fluoro-4-trifluoromethyl)benzyl biguanide;
N1-piperidine-N5-(3-chloro-4-trifluoromethyl)benzyl biguanide;
N1-piperidine-N5-(4-fluoro-3-trifluoromethoxy)benzyl biguanide;
N1-piperidine-N5-(3-fluoro-4-trifluoromethoxy)benzyl biguanide;
N1-piperidine-N5-(3-chloro-4-trifluoromethoxy)benzyl biguanide;
N1-piperidine-N5-(2,6-difluoro)benzyl biguanide;
N1-piperidine-N5-(3,4-difluoro)benzyl biguanide;
N1-piperidine-N5-(2,4-dichloro)benzyl biguanide;
N1-pyrrolidine-N5-(3,4-dichloro)benzyl biguanide;
N1-piperidine-N5-(3,4-dichloro)benzyl biguanide;
N1-piperidine-N5-(thiophene-2-yl)ethyl biguanide;
N1-pyrrolidine-N5-(phenethyl)biguanide;
N1-piperidine-N5-(phenethyl) biguanide;
N1-azepane-N5-(phenethyl) biguanide;
N1-azepane-N5-((4-fluoro)phenethyl) biguanide; or
N1-azepane-N5-((4-chloro)phenethyl) biguanide.

9. The compound of Formula 1 or the pharmaceutically acceptable salt thereof of claim 1, wherein the pharmaceutically acceptable salt is a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzensulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid and boric acid.

10. A method of preparing a compound of Formula 1, comprising:
reacting a compound of Formula 2 with dicyanoamide in at least one organic solvent to obtain a compound of Formula 3; and
reacting the compound of Formula 3 with a compound of Formula 4 in at least one organic solvent to obtain the compound of Formula 1:

[Formula 1]

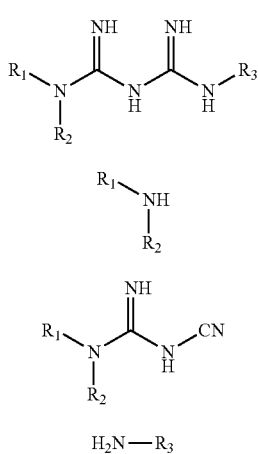

[Formula 2]

[Formula 3]

[Formula 4]

$H_2N—R_3$ wherein $R_1$ and $R_2$ are taken together with nitrogen to which they are attached to form 3- to 8-membered heterocycloalkyl, $R_3$ is $C_{4-7}$ cycloalkyl; or $C_{1-12}$ alkyl unsubstituted or substituted with $C_{3-12}$ aryl or $C_{3-12}$ heteroaryl, wherein $C_{4-7}$ cycloalkyl, 3- to 8-membered heterocycloalkyl, $C_{3-12}$ aryl or $C_{3-12}$ heteroaryl is unsubstituted or substituted with at least one non-hydrogen substituent selected from the group consisting of halogen, $C_{1-4}$ alkyl and $C_{1-4}$ alkoxy, and the non-hydrogen substituent is unsubstituted or further substituted with halogen.

11. A method of preventing or treating a disease comprising:
administering a therapeutically effective amount of a compound of Formula 1 or a pharmaceutically acceptable salt thereof defined in claim 1 to a subject in need thereof, wherein the disease is selected from the group consisting of diabetes mellitus, obesity, hyperlipemia, hypercholesterolemia, fatty liver, coronary artery disease, osteoporosis, polycystic ovary syndrome, metabolic syndrome, cancer, muscle pain, myocyte damage and rhabdomyolysis.

12. The method of claim 11, wherein the diabetes mellitus is insulin-independent diabetes mellitus.

13. The method of claim 11, wherein the treatment of cancer is inhibition of recurrence or metastasis of cancer.

14. The method of claim 11, wherein the cancer is a disease selected from the group consisting of uterine cancer, breast cancer, gastric cancer, brain cancer, colorectal cancer, lung cancer, skin cancer, blood cancer and liver cancer.

15. The method of claim 11, wherein the compound is formulated as a tablet, a capsule, a pill, a granule, powder, an injection or a liquid.

* * * * *